(12) United States Patent
Anderson et al.

(10) Patent No.: US 11,065,431 B2
(45) Date of Patent: Jul. 20, 2021

(54) CAPPING AND CLEANSING DEVICES FOR NEEDLEFREE VASCULAR ACCESS CONNECTORS

(71) Applicant: CleanSite Medical, Inc., Solana Beach, CA (US)

(72) Inventors: Nicholas Anderson, Brooklyn, NY (US); John Grant, Solana Beach, CA (US); Daniel M. Chambers, Solana Beach, CA (US); Adam Ariely, Encinitas, CA (US); David G. Matsuura, Del Mar, CA (US); Philip J. Simpson, Escondido, CA (US)

(73) Assignee: CleanSite Medical, Inc., Solana Beach, CA (US)

( * ) Notice: Subject to any disclaimer, the term of this patent is extended or adjusted under 35 U.S.C. 154(b) by 0 days.

(21) Appl. No.: 16/795,565

(22) Filed: Feb. 19, 2020

(65) Prior Publication Data
US 2020/0197686 A1  Jun. 25, 2020

Related U.S. Application Data

(63) Continuation-in-part of application No. 16/059,029, filed on Aug. 8, 2018.
(Continued)

(51) Int. Cl.
*A61M 39/16* (2006.01)
*A61M 39/20* (2006.01)
*A61M 39/18* (2006.01)

(52) U.S. Cl.
CPC .......... *A61M 39/162* (2013.01); *A61M 39/18* (2013.01); *A61M 39/20* (2013.01); *A61M 2205/0205* (2013.01)

(58) Field of Classification Search
CPC .... A61M 39/162; A61M 39/18; A61M 39/20; A61M 2205/0205; A61M 39/16;
(Continued)

(56) References Cited

U.S. PATENT DOCUMENTS 3,843,006 A * 10/1974 Naito ................... B65D 50/041
215/220
5,554,135 A    9/1996 Menyhay
(Continued)

FOREIGN PATENT DOCUMENTS

WO   WO-2005037362 A1 *  4/2005  ............ A61M 39/26
WO   WO-2010034470 A1 *  4/2010  ............ A61M 39/26

*Primary Examiner* — Shefali D Patel
*Assistant Examiner* — Avery Smale
(74) *Attorney, Agent, or Firm* — Acuity Law Group, P.C.; Daniel M. Chambers

(57) ABSTRACT

Capping and cleansing devices for capping and cleansing needlefree connectors, particularly luer access devices such as needlefree vascular access connectors, and methods for using said devices, are described. The devices of the invention each include interconnected inner and outer housings that a user can transition between a locked or engaged position to allow the inner and outer housings to rotate in unison and an unlocked or disengaged position that allows the outer housing to rotate independently of the inner housing, and a compressible cleansing matrix secured in the devices (preferably in a well in the outer housing).

14 Claims, 13 Drawing Sheets

Related U.S. Application Data

(60) Provisional application No. 62/807,239, filed on Feb. 19, 2019, provisional application No. 62/542,770, filed on Aug. 8, 2017.

(58) Field of Classification Search
CPC ... A61M 39/143; A61M 39/1011; A61L 2/18; A61L 2202/20; A61L 2202/23; A61L 2202/24; F16L 47/16; F16L 37/244; F16L 3/08; A61B 90/70; A61B 2090/701; B65D 59/06

See application file for complete search history.

(56) References Cited

U.S. PATENT DOCUMENTS

| | | |
|---|---|---|
| 5,674,206 A * | 10/1997 | Allton ............... A61M 39/26 604/249 |
| 6,050,978 A * | 4/2000 | Orr ................... A61M 39/26 251/149.1 |
| 7,282,186 B2 | 10/2007 | Lake, Jr. et al. |
| 7,780,794 B2 | 8/2010 | Rogers et al. |
| 7,985,302 B2 | 7/2011 | Rogers et al. |
| 8,172,825 B2 | 5/2012 | Rogers et al. |
| 8,206,514 B2 | 6/2012 | Rogers et al. |
| 8,523,831 B2 | 9/2013 | Solomon et al. |
| 8,740,864 B2 | 6/2014 | Hoang et al. |
| 8,834,650 B2 | 9/2014 | Rogers et al. |
| 8,961,475 B2 | 2/2015 | Solomon et al. |
| 9,114,915 B2 | 8/2015 | Solomon et al. |
| 9,809,355 B2 | 11/2017 | Solomon et al. |
| 10,155,056 B2 | 12/2018 | Solomon et al. |
| 2012/0111368 A1 * | 5/2012 | Rahimy ............. A61M 39/20 134/22.1 |
| 2012/0302997 A1 | 11/2012 | Gardner et al. |
| 2018/0256879 A1 * | 9/2018 | Chiu ................. B08B 9/023 |

\* cited by examiner

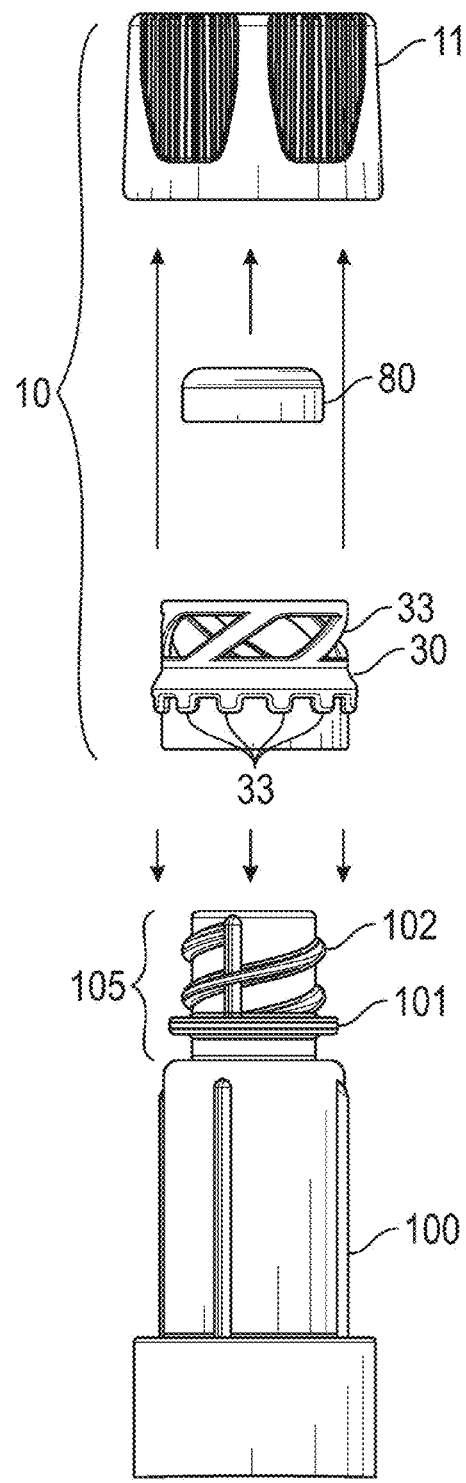

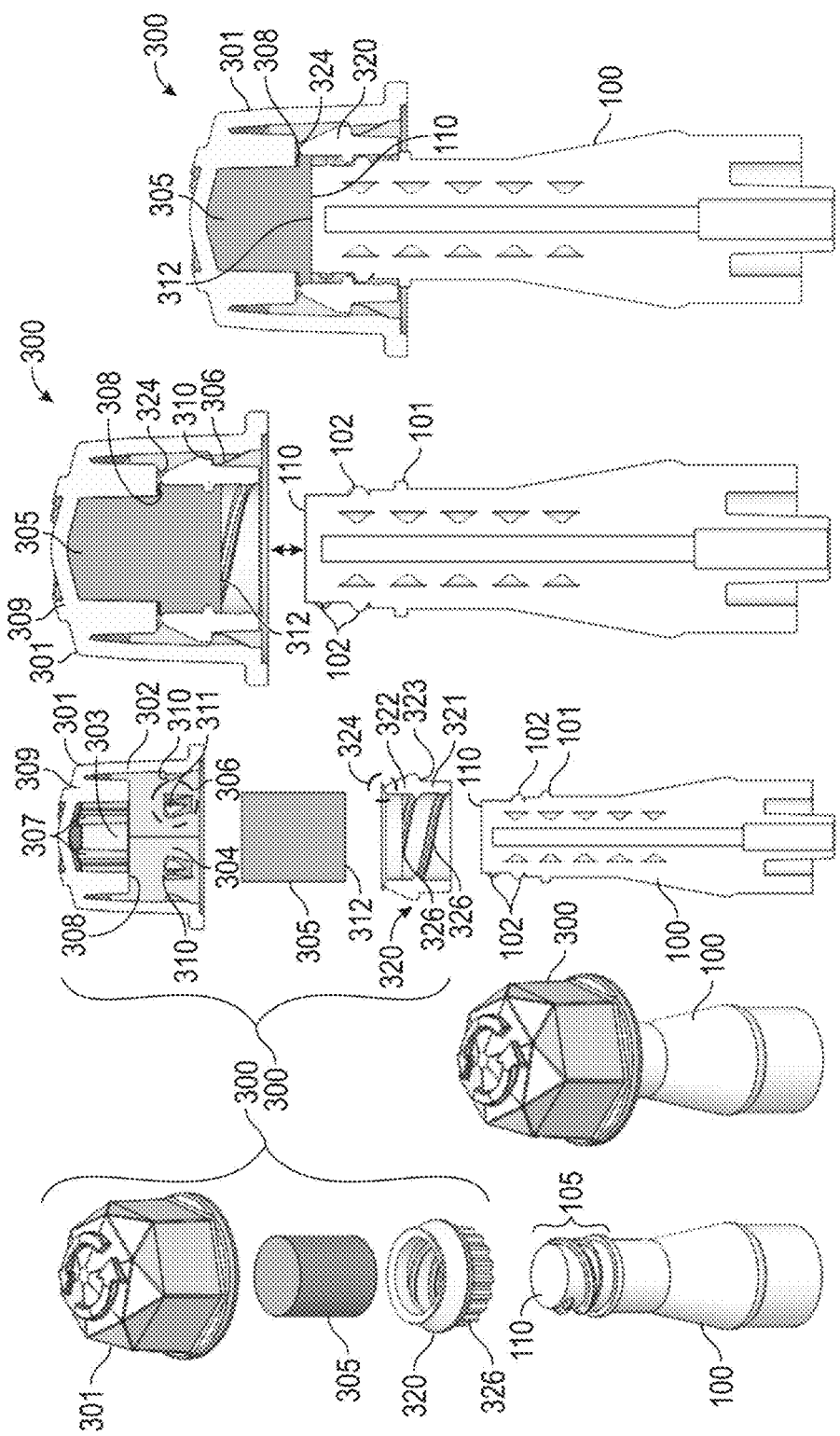

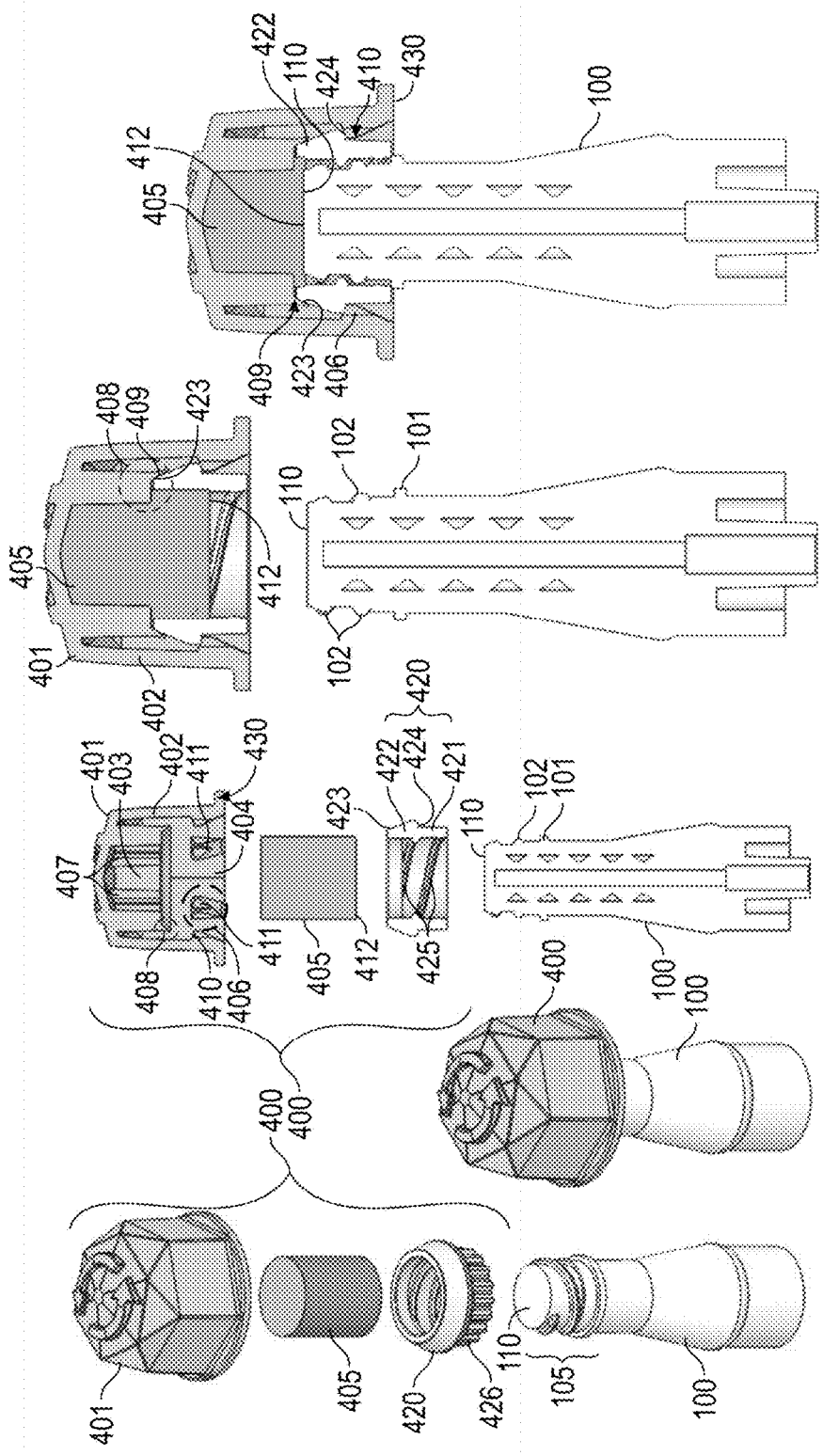

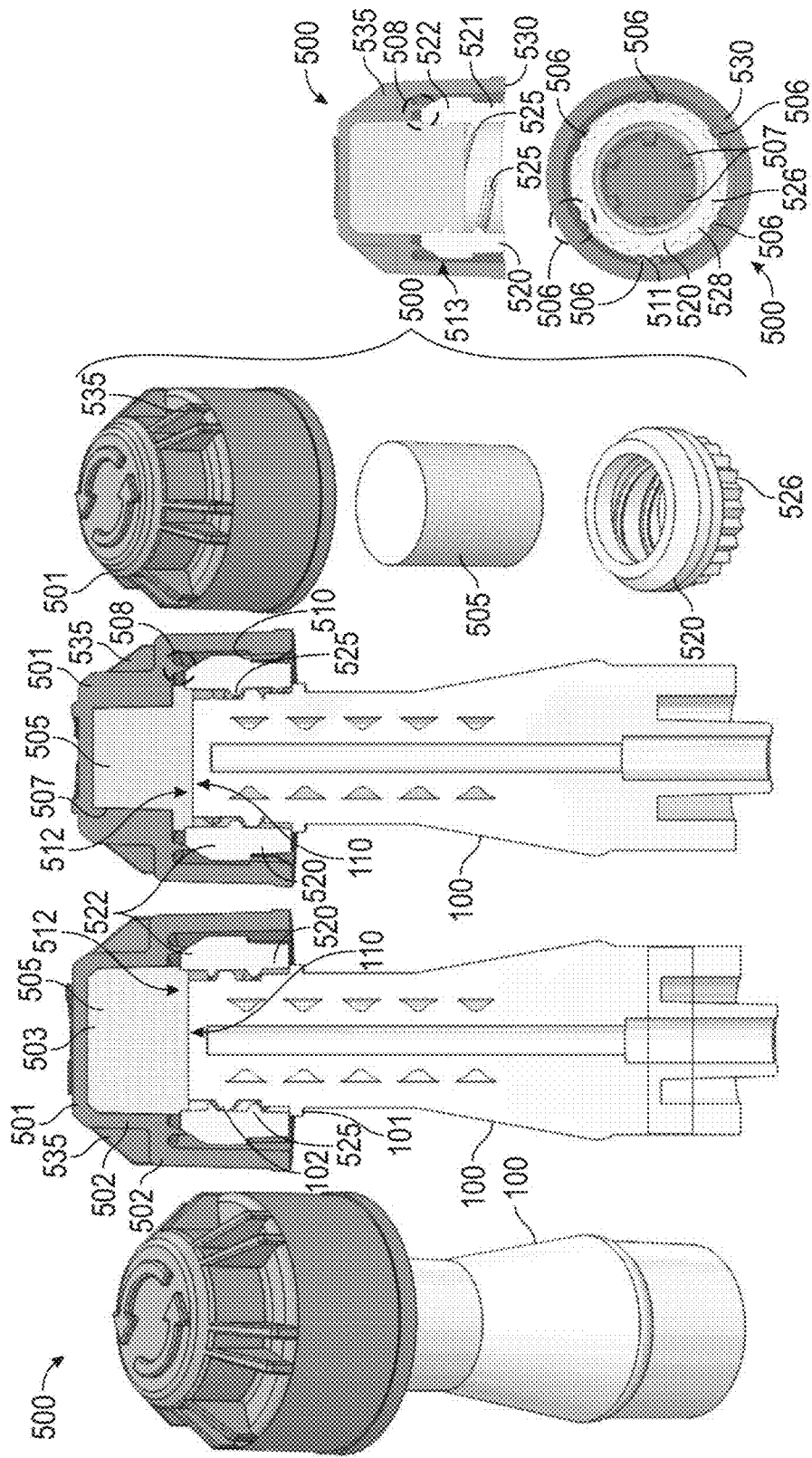

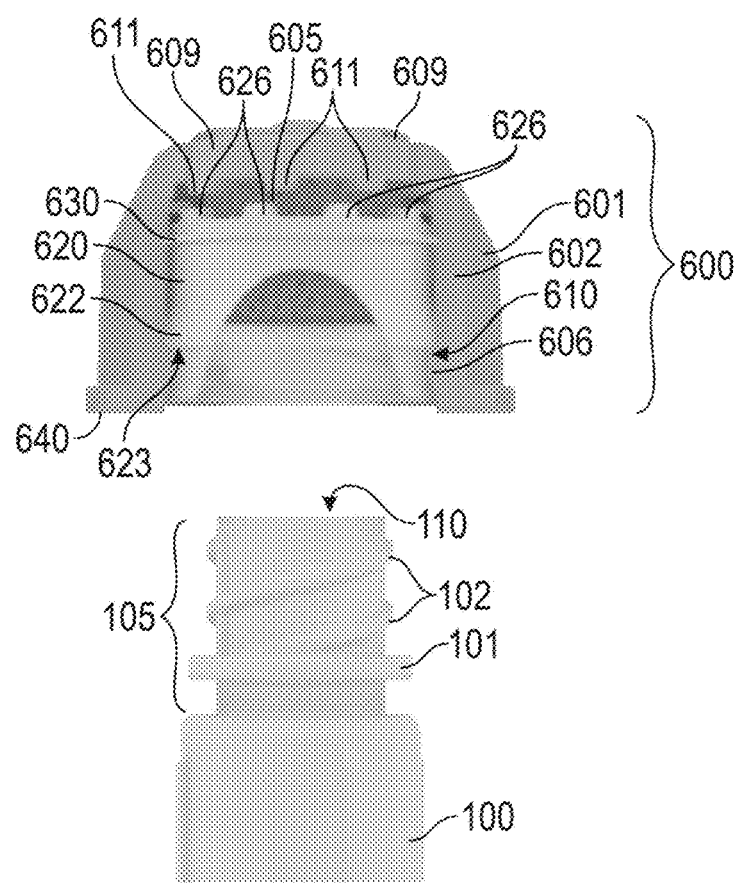

CAPPING AND CLEANSING DEVICES FOR NEEDLEFREE VASCULAR ACCESS CONNECTORS

RELATED APPLICATIONS

This application claims the benefit of and priority to: U.S. provisional patent application No. 62/807,239, filed on 19 Feb. 2019, and is a continuation-in-part of U.S. patent application Ser. No. 16/059,029, filed on 8 Aug. 2018, which claims the benefit of and priority to U.S. provisional patent application No. 62/542,770, filed on 8 Aug. 2017. All of the aforementioned priority applications are hereby incorporated by reference, each in its entirety for any and all purposes.

TECHNICAL FIELD OF THE INVENTION

This invention is directed to cleansing devices for cleansing and capping medical devices, particularly luer access devices such as needlefree, valved connectors (NCs), and methods for making and using such articles.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

In the medical field, and in particular the area of infusion of fluids or aspiration of fluids to or from a patient, there remains a need to prevent the transmission of pathogens into or onto a patient from a potentially contaminated surface of a medical device such as a luer access device, for example, a needlefree, valved connector (NC). Pathogens include microorganisms such as bacteria, fungi, and viruses, the transmission of which into a patient may result in an infection that could be life-threatening. Specific to healthcare settings, the term "nosocomial infection" describes those infections that originate from or occur in a hospital or hospital-like setting. In the U.S., nosocomial infections are estimated to occur in at least 5% of all acute care hospitalizations. The estimated incidence is more than two million cases per year, resulting in significant morbidity, mortality, and an expense. Indeed, nosocomial infections are estimated to more than double the mortality and morbidity risks of any admitted patient, and likely result in about 100,000 deaths a year in the United States alone. Common sites for the transmission of contaminating microorganisms into a patient's bloodstream are found on medical devices such as luer access devices, vials, needlefree (or needle free) valves, and the injection ports of vessels, tubing, and catheters. The incidence of such infections in patients is increasing, and infection control practitioners (ICPs) often cite improper cleansing of sites as a major source of such infections.

As described above, patient exposure to pathogens and infectious reagents (e.g., pathogenic bacteria, viruses, fungi, etc.) in medical settings (e.g., hospitals, out-patient surgery centers, home-care settings, etc.) is a matter of serious concern. One route of exposure to such reagents is the opening made in skin provided by the bore of needle, cannula, or other similar device used to provide access to a patient's vasculature. It is known that patients whose skin has been compromised in this way are at increased risk for developing serious blood stream infections. In the United States alone, approximately 300,000 blood stream infections per year result from the installation and use of peripheral intravenous catheters (PIVC), and more than 80,000 blood stream infections are associated with the use central venous catheters (CVC). All told, in the U.S. approximately 28,000 patients die annually from hospital-acquired infections that result from PIVC and CVC use, and many times that number are made seriously ill but survive. Costs associated with the care and treatment of patients that develop infections due to PIVC and CVC use is estimated to exceed $4 billion annually in the U.S. alone.

In hospital settings today, occupational health and safety regulations designed reduce the risk to health care workers from needle stick and similar injuries have resulted in the deployment of needlefree medical valves (also referred to herein as "needlefree connectors" or "NCs") whenever possible. Currently, more than 1 billion NCs are used annually in hospitals throughout the U.S. Needlefree connectors are used primarily in conjunction with PIVC and CVC devices and associated IV administration and extension sets, which may contain from as few as one to as many as 3, 4, 5, or more NCs. FIG. 2A illustrates an example of a representative NC in use today.

The widespread use of needlefree connectors in acute medicine has contributed to a marked increase in the incidence of hospital-acquired infections (HAIs), particularly blood stream infections (BSIs). To reduce the risk of infection from a needlefree connector contaminated with microorganisms, standard practice today requires that a nurse or other healthcare worker clean (or "scrub") the surface of NC by vigorously rubbing those of its exterior surfaces in the fluid path with a sterile alcohol swab or wipe immediately prior to making a fluid connection to the NC, for example, by attaching a syringe to the NC's threaded valve portion to deliver a medication via a PIVC already connected to the patient. Given the magnitude of the mortality and morbidity associated with HAIs, particularly with regard to central line-associated blood stream infections (CLABSIs), and the large number of blood stream infections that result from PIVC and CVC use (so-called "peripheral line—associated blood stream infections (PLABSIs) and central line-associated blood stream infections (CLABSIs), respectively), a long-recognized yet significant unmet need exists for articles or devices that can be used to reduce or eliminate the risk of initiating an HAI merely by accessing a patient's vasculature through a needlefree valve component of a PIVC or CVC inserted into a blood vessel of a patient.

Traditionally, and as noted above, cleaning, cleansing, or disinfecting a potentially contaminated NC surface involved a protocol of alcohol swabbing prior to making the necessary connections to the site. Alcohol swabs are typically small pads of cotton gauze soaked in isopropyl alcohol (IPA), packed individually in foil packages to prevent evaporation of the IPA from the swab prior to use. Properly used, the package is opened at or near the site to be swabbed. With gloved hands, the swab is removed by a nurse or other healthcare provider and used to scrub the top and side surfaces of the valve portion of the NC to be connected. After use, the swab and foil package are discarded and the cleansed valve portion of the NC is allowed to dry, usually 20-30 seconds, immediately prior to making any connection.

This "drying" period is important because, as the IPA dries, it breaks open the cellular walls of microorganisms, thereby killing them.

Unfortunately, because of increased duties and responsibilities, shrinking nursing staffs, and inadequate training, alcohol swabbing (or scrubbing) is often not performed or is poorly executed. A poorly swabbed site can carry microorganisms that, if allowed to enter a patient's body, can cause serious, and potentially life-threatening, infection. In addition, supervisory oversight is nearly impossible, because unless a supervisor actually observes swabbing as it is performed, the supervisor cannot know whether or not the scrubbing procedure was done properly or performed at all. Indeed, reported compliance with such "scrub the hub" protocols has been as low as 10%. Further, without at least a sufficient microscopic examination for microbial residue (e.g., biofilm), there may be no evidence of "scrubbing the hub" being performed.

Thus, a significant need still exists for devices and techniques cleanse sites on medical devices prior to their use with or connection to patients, and which eliminate technique-related and training issues and provide an unequivocal indicator that a site is clean prior to accessing a patient's vascular system.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

As used herein, the singular forms "a", "an", and "the" include plural references unless the context clearly dictates otherwise.

As used herein, the term "about" refers to approximately a +/−10% variation from the stated value. It is to be understood that such a variation is always included in any given value provided herein, whether or not it is specifically referred to.

A "patentable" composition, process, machine, or article of manufacture according to the invention means that the subject matter at issue satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The term "species", when used in the context of describing a particular compound or molecule species, refers to a population of chemically indistinct molecules.

SUMMARY OF THE INVENTION

The object of the invention is to address these long-standing but still unmet needs. This invention addresses these needs by providing patentable, single-use cleansing (disinfecting) and capping devices or articles that can be used to effectively and efficiently cleanse/disinfect and cap, and preferably sterilize, exposed surfaces of medical articles such as luer access devices, particularly needlefree connectors, particularly the accessible surface(s) of the threaded valve portions of needlefree connectors, particularly those surfaces (valve surfaces, threads, etc.) that may become contaminated with pathogens or other infectious reagents and which form part of the fluid communication pathway between an external fluid source (e.g., a medicine filled syringe with a male luer fitting, an IV bag, etc.) and a patient's blood stream. In the context of the invention, "cleanse" encompasses cleaning, disinfecting, sanitizing, and/or sterilizing, whereas "capping" refers to using a device, i.e., a "cap", to cover a surface, or set of surfaces, of an NC so as to limit or prevent exposure of such surface(s) to the environment (e.g., the air circulating in a hospital's intensive care unit, the microbiome resident on a patient's skin, clothing, bedding, unclean fingers, etc.) for a period longer than necessary to cleanse the desired surface(s) of a needlefree connector.

Thus, in one aspect, the invention provides capping and disinfecting devices for medical devices such as luer access devices, including needlefree, valved vascular access connectors (NCs). In general, such devices include an inner housing configured to allow the device to be screwed onto and unscrewed from the threaded valve portion of an NC, an outer housing that retains the inner housing but which a user can, when desired, rotate independently of the inner housing to provide scrubbing or disinfecting action, and a compressible cleansing matrix preferably impregnated with a disinfectant, for example, a 70% IPA solution. The device also preferably includes an easily removable seal to maintain sterility and prevent loss of the disinfectant after the device is assembled until such time as it is used in the field to outer housing and cleanse an NC.

The devices of the invention include an inner housing. In some preferred embodiments, the inner housing is comprised of a sidewall that bounds a central, interior (preferably cylindrical) bore that spans between oppositely disposed first and second (or upper and lower, respectively) openings. In many of these embodiments, the first (upper) opening is sized to allow the compressible cleansing matrix resident at least in part in a matrix well or otherwise attached to the inner surface of the outer housing to protrude into and through the opening into the inner housing's central bore so that the compressible cleansing matrix can engage one or more exterior surfaces of a needlefree connector when the capping and cleaning device is secured to the connector. The second (lower) opening of the inner housing is sized to allow the threaded valve portion of a needless connector to be capped and/or cleansed to be inserted into capping and cleansing device of the invention. The interior wall of the inner housing's central bore includes one or more thread-engaging tabs (or threads), preferably two (or more) oppositely disposed (or otherwise spaced) thread-engaging tabs, preferably near the lower opening. The thread-engaging tab(s)(or threads) is(are) configured to engage a complementary threaded region on the exterior surface of, for example, a needlefree connector such that the capping and cleansing device can, via association of the thread tabs or threads on the interior of the inner housing's central bore with complementary threads on the threaded portion of a needlefree connector, be securely threaded onto (or otherwise removably connected with) the targeted threaded portion of a needlefree connector for capping and, if desired, cleansing.

In some preferred embodiments, the outer surface of the inner housing includes an outer housing-retaining region that includes one or more structures, for example, a circumferential flange (or spaced flange elements), that allow the inner housing to be retained in the outer housing via association with one or more complementary structures (e.g., a circumferential flange (or spaced flange elements) or other suitable engaging elements) on the inner surface of the sidewall of the outer housing. Preferably, such configurations of complementary retaining elements also allow for smooth, low friction movement (i.e., rotation) of the inner and outer housings in relation to each other during certain operations, for example, during a disinfection procedure of a needlefree connector. In some of these embodiments, the retaining element(s) of the inner housing can mechanically engage an adjacent region on the inner surface of the sidewall of the outer housing, for example, when a user squeezes or otherwise applies sufficient force to the outer housing to deform it so as to allow engaging regions on the inner surface of the outer housing to engage corresponding engaging regions on the exterior surface of the inner housing so as to allow the inner and outer housings to rotate in unison (as would occur, for example, when a user attaches or removes a device from an NC). In some of these embodiments, the retaining element(s) of the inner housing can also serve as engaging elements with complementary regions, features, or structures on the inner surface of the sidewall of the outer housing adjacent or otherwise in close proximity thereto. In other embodiments, the outer surface of the inner housing further includes one or more outer housing engaging elements or regions designed to associate with one or more inner housing engaging elements or regions disposed on the interior or inner surface of the outer housing. Examples of such elements include, for example, a circumferential band of spaced teeth or teeth-like elements protruding from the exterior surface of the inner housing and positioned below the outer housing-retaining region (e.g., a circumferential flange), which teeth (or other suitable engaging structures) can be engaged by complementary structures arrayed on the interior surface of the outer housing when the housings are assembled into a functional subassembly.

In other preferred embodiments, the upper exterior surface of the inner housing includes an outer housing-engaging region that includes one or more structures that allow the inner housing to mechanically engage complementary structures (e.g., pawls or other suitable engaging elements) on the inner surface of the top of the outer housing so that when the complementary engaging elements of the outer housing and inner housing are brought into close proximity the engaging elements of the outer housing and inner housing engage, allowing the outer housing and inner housing to rotate in unison. Certain preferred embodiments of outer housing-engaging structures include spaced teeth (or other suitable engaging elements) arrayed on the top or upper surface of the inner housing's preferably cylindrical sidewall. As will be appreciated, when such inner and outer housing engaging elements are unmated or disengaged, a user can rotate or spin the outer housing in relation to the inner housing, as is, for example, done during a cleansing or disinfecting operation of the needlefree connector to which the device of the invention is attached. Thus, when the capping and cleansing device is secured to a needlefree connector, when such engaging elements are not functionally associated (or mated or otherwise engaged), a user can rotate the outer housing (and compressible cleansing matrix) in relation to the inner housing and connected needlefree connector. On the other hand, when the complementary elements on the inner surface of the top of the outer housing and the upper surface of the top of the inner housing are engaged (in whole or even partially), such as when a user applies downward pressure to the device to place it on or remove it from a needlefree connector, the inner and outer housings rotate together, allowing, for example, the capping and cleansing device to be attached to or removed from the NC.

In some preferred embodiments, the inner housing also includes an NC sealing member configured to provide a fluid tight seal between the capping and cleansing device of the invention and a needlefree connector connected thereto. In some embodiments the NC sealing member is an O-ring (or comparable seal) preferably disposed in a channel formed in the inner surface of the wall of the inner housing proximate to the second (lower) opening, typically below the thread-engaging tab(s)(or threads).

The devices of the invention also include an outer housing adapted or configured to retain the inner housing therein such that, when the device is attached to a needlefree connector, under certain conditions the outer housing can rotate (preferably about its central axis) in relation to the inner housing. Any suitable configuration of complementary mechanical or structural features or elements on facing or opposing surfaces can be used to provide retention of the inner housing inside the outer housing's main cavity and to allow for engagement and disengagement of the outer housing from the inner housing in order to allow the outer housing to be rotated in relation to the inner housing when the device is attached to a needlefree connector and a user desires to cleanse the corresponding surface(s) of the NC using the capping and cleansing device of the invention.

In some embodiments, when the device of the invention is attached to a needlefree connector, the inner and outer housings adopt a disengaged, neutral, or rotating configuration relative to each other such that a user can rotate the outer housing in relation to the inner housing to perform a cleansing operation on the valve portion of the NC to which the device is attached. Such a disengaged, neutral, or rotating configuration can be achieved by any suitable approach, including by providing complementary engaging elements or structures on adjacent surfaces of the inner and outer housings that under certain conditions, for example, when the outer housing is pulled up, pushed down, or squeezed by a user in relation to the inner housing, engage each other; otherwise the engaging elements remain disengaged, which allows rotation of the outer housing in relation to the inner housing when the device is secured to an NC. Features that allow transitioning between engaged and disengaged positions include springs or biasing or resilient elements or materials. In other embodiments, when the device is attached to a needlefree connector, the inner and outer housings adopt an engaged configuration relative to each other such that they rotate in unison unless a user applies sufficient force to the outer housing to cause the engaging elements to disengage and thus allow the outer housing to be rotated independently of the inner housing.

The outer housing includes a cylindrical cavity designed to receive and retain the inner housing using one or more features or elements that allow the outer housing to be rotated in relation to the inner housing if and when desired. The cavity is formed by a curved outer sidewall that in some embodiments is joined to a top portion of the housing about its periphery and which also preferably has a concentric central matrix well or matrix attachment region to or with which the compressible cleansing matrix is attached or otherwise associated, although in some embodiments some degree of eccentricity between the matrix well and central rotational axis of the outer housing may be desired. In some embodiments, the outer housing is formed by a sidewall that is tapered and/or has one or more steps.

In some preferred embodiments, the inner surface of the top of the outer housing includes one or more inner housing engaging elements or structures (e.g., teeth) designed to releasably engage complementary structures in the outer housing-engaging region on the top of the inner housing. Engagement of the outer housing's inner housing engaging structure(s) with those in the outer housing-engaging region of the inner housing allow a user to rotate the outer housing and inner housing in unison, for example, as a capping and cleansing device's inner housing is screwed onto the threaded portion of a needlefree connector to be cleansed and/or capped. Once the device is releasably secured to a needlefree connector via the inner housing, the outer housing's inner housing engaging elements or structure(s) can be (or are) disengaged from the outer housing-engaging elements of the inner housing, for example, by the biasing action or resilience of a the compressible cleansing matrix, thereby allowing a user to rotate the outer housing about its central axis in relation to the inner housing. A representative example of such engaging structures is shown in published US patent application publication no. 2018/0304067, although features such as an inner housing having an opening in its top to allow a compressible cleansing matrix attached to the inner surface of the top of the outer housing to extend into the bore of the inner housing so that it can contact surfaces of a needlefree connector upon connection of the former to the latter are also envisioned.

In some of these embodiments, the outer housing may include one or more vents to allow fluid and/or air from inside the device to escape as the capping and cleansing device is secured to a needlefree connector, while in other embodiments, no vent(s) is(are) provided. In embodiments with one or more vents, a membrane, filter, or other permeable or semi-permeable barrier may be employed to allow a unidirectional or bidirectional flow of air, gas, or vapor through the vent(s) but prevent the movement of microorganisms (e.g., bacteria, fungi, viruses, etc.) into the capping and cleansing device of the invention.

In certain preferred embodiments, the outer surface of the outer housing of a capping and cleansing device according to the invention includes one or more grip-enhancing structures (e.g., a plurality of vertical ridges) or coatings. Such grip-enhancing structures or coatings facilitate a user's grasp of the housing of a capping and cleansing device between her/his fingers, which can be helpful not only during insertion and removal of a needlefree connector from the capping cleansing device, but also during the cleansing process, where the user rotates the outer housing in relation to the inner housing in order to scrub and thereby clean or cleanse the surface(s) of the inserted needlefree connector with the compressible cleansing matrix of the device.

In some preferred embodiments, the devices of the invention include one or more elements or features arrayed on facing surfaces of the inner and outer housings that allow a user to sense that the outer housing is rotating in relation to the inner housing in order to provide cleansing action on the valve surface of the NC to which the device is attached. Such sensory feedback can include one or more of auditory, tactile, and/or visual stimuli generated from the device by rotation of the outer housing in relation to the inner housing.

In the devices of the invention, the inner and outer housings are manufactured separately by any suitable process, for example, 3D-printing, injection molding, etc., and then assembled into a two-part subassembly in which the inner housing is retained within the main cavity of the outer housing by one or more complementary retaining elements, features, or structures on each housing. The inner and outer housings also include complementary mechanical or structural engaging elements, features, or structures on one or more interfacing surfaces that can be engaged and disengaged so as to allow the inner and outer housings to rotate together or to allow the outer housing to rotate independently of the inner housing. In this way, the inner and outer housings can be associated such that they can rotate in unison, allowing a user to thread (or screw) the device onto or remove (unscrew) it from the threaded valve portion of an NC if and when desired, while also making it possible for a user to rotate the outer housing in relation to the inner housing, thereby allowing the compressible cleansing matrix to effectively scrub or cleanse the region(s) of a threaded valve portion of an NC to which it is attached. In certain preferred embodiments, the inner and outer housings further include complementary mechanical or structural housing sealing elements, features, or structures on one or more interfacing surfaces that allow formation of seal between adjacent surfaces of the inner and outer housings, which seal is preferably substantially fluid tight but does not substantially hinder or inhibit rotation of the outer housing in relation to the inner housing during performance of a cleansing procedure or process by a user. In some embodiments, the inner housing may also include a seal that interacts with the needlefree connector to form an additional or alternate seal.

A capping and cleansing device of the invention also includes a compressible cleansing matrix disposed therein. In most embodiments, the compressible cleansing matrix is disposed in a matrix well or the like in the interior of the outer housing, although any suitable retaining configuration can be employed that allows the compressible cleansing matrix to rotate in conjunction with rotation of the outer housing so as to provide the capability of using the compressible cleansing matrix to scrub or otherwise clean, cleanse, or disinfect the surface(s) of the valve region of a needlefree connector. As will be appreciated, the compressible cleansing matrix is positioned to contact one or more exterior surface(s) of an NC connected to the capping and cleansing device. The compressible cleansing matrix, for example, an open-cell or felted foam, is preferably retained in the matrix well by one or more matrix retaining elements, which element(s) assist in retention of the compressible cleansing matrix in the matrix well in addition to transmission of rotational forces from the outer housing to the compressible cleansing matrix as occurs during a procedure to disinfect or cleanse a needlefree connector. As will be appreciated, during such rotation (of the outer housing and compressible cleansing matrix), the compressible cleansing matrix also rotates in relation to the inner housing when the outer housing is rotated during a procedure to disinfect or cleanse a needlefree connector. The compressible cleansing matrix attached to or otherwise associated with the outer housing can be axially compressed (i.e., compressed along the central axis of the outer housing's matrix well) upon insertion of a needlefree connector into such a capping and cleansing device.

Because the needlefree connector surface(s) to be cleansed may be contaminated with microorganisms that form a biofilm (i.e., a matrix of microorganisms and extracellular material attached to a surface, which enables the microorganisms, typically bacteria and/or fungi, to adhere to a surface and carry out certain biochemical processes), the compressible cleansing matrix also preferably has sufficient mechanical integrity when compressed and rotated to allow it to disrupt any biofilm that may be present on the surface of the needlefree connector, as can occur by rotating, twisting, or otherwise moving the then-compressed cleansing matrix in relation to the needlefree connector, for example, by rotating the outer housing (to which the compressible cleansing matrix is attached) in relation to the inner housing of the capping and cleansing device and the needlefree connector to which inner housing is releasably attached. The resulting friction between the compressed cleansing matrix and surface of the needlefree connector disrupts the biofilm, thereby cleansing, and preferably sterilizing, the needlefree connector. Leaving the capping and cleansing device secured to (i.e., capping) the needlefree connector after such a cleansing operation will limit, and preferably preclude, biofilm regrowth and/or the microbial recolonization of cleansed surfaces (which remain in contact with the compressible cleansing matrix).

In preferred embodiments, the compressible cleansing matrix includes one or more cleansing reagent species dispersed therein, preferably at the time the device is manufactured, although in some embodiments, the cleansing reagent may be dispersed into the matrix just prior to the matrix coming into contact with a needlefree connector. In embodiments of the latter sort, the cleansing reagent is preferably housed in the housing of the capping and cleansing device in a reservoir configured to be ruptured just prior to performance of a cleansing operation. In some embodiments, the capping and cleansing device of the invention will include a valve or opening to allow liquid in the cleansing reagent to evaporate.

In some preferred embodiments, the compressible cleansing matrix includes two or more components. In some of such embodiments, one component of the matrix is attached to the inner surface of the outer housing and another component is secured to the inner surface of the wall forming the inner housing, preferably between protruding threaded regions adapted to engage complementary threads on a needlefree connector. If present, the component of the compressible cleansing matrix secured to the inner surface of the inner housing wall is preferably configured to radially compress upon association with a needlefree connector to be capped and cleansed.

In preferred embodiments, the capping and cleansing devices of the invention include a removable lid or seal attached to the outer housing to seal the device, thus separating the interior spaces and structures of the inner and outer housings from the external environment. Such a lid or seal prevents exposure of the device's interior, including the inner housing and compressible cleansing matrix, to the environment until the removable (preferably, peelable) lid or seal is removed, typically by a healthcare worker just prior to her/his use of the capping and cleansing device to clean, cleanse, or disinfect a needlefree connector to which a fluid connection is to be made. In preferred embodiments, such cleansing substantially disrupts any microbial contamination, for example, microbial biofilm or other microbial contamination that may exist on surfaces contacted by the compressible cleansing matrix. If desired, the capping and cleansing device can be left in place (typically after cleansing the needlefree connector attached thereto) in order to cap the needlefree connector until it is further accessed, thereby minimizing exposure of capped exterior surfaces of the NC to potential pathogen contamination (and biofilm formation) from the surrounding environment. Lids or seals are typically installed during manufacture of a capping and cleansing device of the invention. In those embodiments where the capping and cleansing devices are sterilized during manufacture (e.g., by irradiation, exposure to ethylene oxide, etc.), lids or seals are preferably applied prior to packaging and sterilization.

In some preferred embodiments, the devices of the invention are sealed individually, while in other embodiments, 2-20 or more devices are sealed onto a single piece of lidding or sealing stock, after which they may be separated into individual sealed products or maintained in strip form, as a strip format having multiple devices all sealed to a single strip is a convenient format for use in healthcare environments, where such strips can be hung, for example, from an IV pole at a patient's bedside. After sealing and packaging, the devices of the invention are sterilized using any suitable sterilization method (e.g., gamma or e-beam irradiation, treatment with ethylene oxide, etc.) compatible with the materials used to manufacture the particular device(s) of the invention.

Other aspects of the invention concern methods of cleansing and/or capping needlefree connectors using a capping and cleansing device according to the invention. Such methods typically involve disengaging the engaging elements of the outer housing and inner housing after it has been connected to a needlefree connector, thus allowing a user to rotate or spin the outer housing in relation to the inner housing and needlefree connector to which the device of the invention is secured. Such disengagement does not impair contact between the device's compressible cleansing matrix and the associated surface(s) of the needlefree connector. Spinning or rotation of the outer housing in relation to the inner housing, and the associated surface(s) of the needlefree connector, allow those surfaces to be scrubbed, thereby cleansing them. Preferably, such cleansing methods provide for the disruption of any biofilm present on the surface(s) of the needlefree connector associated the capping and cleansing device. And in those embodiments where the compressible cleansing matrix contains one or more antimicrobial reagents, microbes and pathogens present in such biofilm and/or on such surface(s) are preferably destroyed or rendered nonviable.

Features and advantages of the invention will be apparent from the following detailed description, and appended claims.

BRIEF DESCRIPTION OF THE DRAWINGS

These and other aspects will now be described in detail with reference to the following drawings. Unless otherwise indicated, it is understood that the drawings are not to scale, as they are intended merely to facilitate understanding of the invention as opposed to specific dimensions, etc. In the drawings, like numbers in two or more drawings represent like elements.

FIG. 2A-FIG. 2D shows an exploded view (a) of a representative capping and cleansing device of the invention and a needlefree connector and several cross-sectional views ((b)-(d)) of a sealed representative capping and cleansing device of the invention (view (b)) and such a capping and cleansing device capping a needlefree connector (views (c) and (d)).

FIG. 7A-FIG. 7E shows five different views of another representative capping and cleansing device of the invention. FIG. 7A shows an exploded perspective view of the device (outer housing, compressible cleansing matrix, and inner housing) and an NC to which the device is to be connected (see FIGS. 7B, 7E). FIG. 7B shows a perspective view of the assembled device depicted in FIG. 7A secured to the threaded region of the valve portion of the NC depicted in FIG. 7A. FIG. 7C shows an exploded cross-section view of the components depicted in FIG. 7A, while in FIG. 7D, the cross section view shows the components of the device of the invention (outer housing, compressible cleansing matrix, and inner housing) assembled into a functional capping and cleansing device ready for attachment to the threaded region of the valve portion of the NC depicted in FIG. 7A. FIG. 7E is a cross section showing the capping and cleansing device of the invention screwed onto the NC, which results compression of the compressible matrix against the NC's valve surface.

FIG. 8A-FIG. 8E shows five different views of another representative capping and cleansing device of the invention. FIG. 8A shows an exploded perspective view of the device (outer housing, compressible cleansing matrix, and inner housing) and an NC to which the device is to be connected (see FIGS. 8B, 8E). FIG. 8B shows a perspective view of the assembled device depicted in FIG. 8A secured to the threaded region of the valve portion of the NC depicted in FIG. 8A. FIG. 8C shows an exploded cross-section view of the components depicted in FIG. 8A, while in FIG. 8D, the cross section view shows the components of the device of the invention (outer housing, compressible cleansing matrix, and inner housing) assembled into a functional capping and cleansing device ready for attachment to the threaded region of the valve portion of the NC depicted in FIG. 8A. FIG. 8E is a cross section showing the capping and cleansing device of the invention screwed onto the NC, which results compression of the compressible matrix against the NC's valve surface.

FIG. 9A-FIG. 9E shows five different views of another representative capping and cleansing device of the invention, with FIG. 9A showing a perspective view of the device secured to the threaded region of the valve portion of an NC. FIGS. 9B and 9C each show an exploded cross-section view of the device/NC assembly shown in FIG. 9A, the difference being that the view depicted in FIG. 9C is slightly rotated about the central axis of the device/NC assembly as compared to the view depicted in FIG. 9B. FIG. 9D shows an exploded perspective view of the device (outer housing, compressible cleansing matrix, and inner housing) depicted in FIGS. 9A-9C. FIG. 9E shows a side cross-section and a bottom view of the device depicted in FIGS. 9A-9D.

FIG. 10A-FIG. 10C shows three different cut-away views of another representative capping and cleansing device of the invention. FIGS. 10B and 10C show the device secured to the threaded region of the valve portion of an NC, while FIG. 10A shows the device disconnected from the NC. FIG. 10B shows the outer housing of the device in a neutral position (the engaging elements of the inner and outer housings are not engaged), from which a user could rotate the outer housing (and compressible cleansing matrix) in relation to the inner housing and NC, to which the inner housing is secured. As will be appreciated, the compressible matrix can serve as a spring that, in the absence of a sufficient counteracting downward force, pushes the outer housing up in relation to the inner housing, allowing a user to rotate the outer housing (and compressible cleansing matrix) in relation to the inner housing and NC is and when desired. Absent such rotation, while connected to the NC the capping and cleansing device of the invention serves as a cap to protect the threaded valve region of the NC from environmental contamination, including microbial contamination. FIG. 10C depicts the device when the engaging elements of the inner and outer housings are engaged, allowing the device to be screwed onto or off of the NC.

Figure 1A:
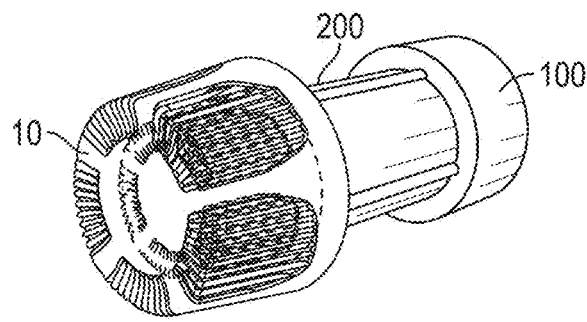
FIG. 1A-FIG. 1H shows several drawings ((a)-(h)) of a representative capping and cleansing device of the invention, its constituent parts (views (b)-(h)), and the device associated with a needlefree connector (view (a)).
Figure 1B:
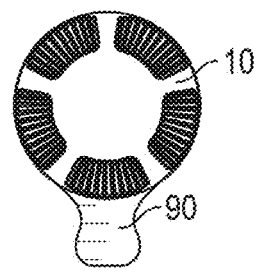
Figure 1C:
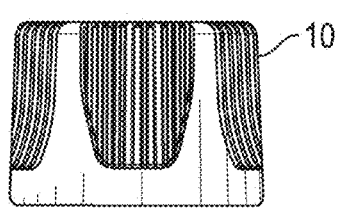
Figure 1D:
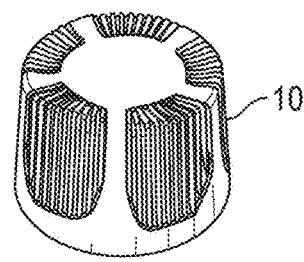
Figure 1E:
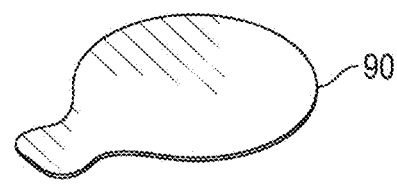
Figure 1F:
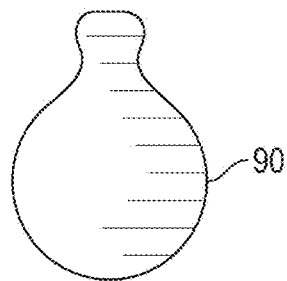
Figure 1G:
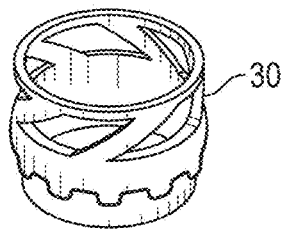
Figure 1H:
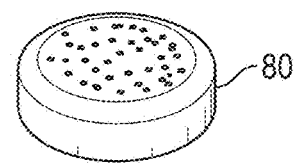

The details of one or more embodiments are set forth in the accompanying drawings and the description below. Other features and advantages will be apparent from the description and drawings, and from the claims.

DETAILED DESCRIPTION

In the following detailed description, reference is made to the accompanying figures (FIGS. 1A-10C), which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

This invention concerns patentable single-use capping and cleansing devices that can be used to effectively and efficiently clean, disinfect, and preferably sterilize, exposed surfaces of needlefree connectors, particularly those of luer access devices such as needlefree medical valves that at times become part of a fluid communication pathway for introduction of fluids (e.g., IV fluids, blood, plasma, medicines, etc.) into a patient, as these surfaces are at risk for contamination with pathogens and infectious reagents such as bacteria, fungi, and viruses. "Single-use" (or "single purpose") refers to an article or device suitable for one use or purpose only, as distinguished from "dual" or "multiple" use or purpose devices. Thus, in the context of the invention, a "single-use" capping and cleansing device is one that is useful for cleansing, for example, a needlefree medical valve. After the cleansing operation, the device may, if desired, be left in place on the needlefree connector until a subsequent fluid connection is made in order to prevent recontamination of the connector's cleansed surface(s), as would occur if the capping and cleansing device of the invention was removed immediately following "scrubbing" of the connector without a fluid connection then being made. After removal, the device of the invention is preferably discarded. Prior to removal, however, the capping and cleansing device can again be used to cleanse the capped surface(s) of the needlefree connector.

In general, a capping and cleansing device of the invention include an inner housing configured to allow the device to be screwed onto and unscrewed from the threaded valve portion of an NC, an outer housing that retains the inner housing but which a user can, when desired, rotate independently of the inner housing to provide scrubbing or disinfecting action, and a compressible cleansing matrix preferably impregnated with a disinfectant, for example, a 70% IPA solution. The device also preferably includes an easily removable seal to maintain sterility and prevent loss of the disinfectant after the device is assembled until such time as it is used in the field to outer housing and cleanse an NC.

In general, such devices include an inner housing configured to allow the device to be screwed onto and unscrewed from the threaded valve portion of an NC, an outer housing that retains the inner housing but which a user can, when desired, rotate independently of the inner housing to provide scrubbing or disinfecting action, and a compressible cleansing matrix preferably impregnated with a disinfectant, for example, a 70% IPA solution. The device also preferably includes an easily removable seal to maintain sterility and prevent loss of the disinfectant after the device is assembled until such time as it is used in the field to outer housing and cleanse an NC.

The devices of the invention include an inner housing. In some preferred embodiments, the inner housing is comprised of a sidewall that bounds a central, interior (preferably cylindrical) bore that spans between oppositely disposed first and second (or upper and lower, respectively) openings. In many of these embodiments, the first (upper) opening is sized to allow the compressible cleansing matrix resident at least in part in a matrix well or otherwise attached to the inner surface of the outer housing to protrude into and through the opening into the inner housing's central bore so that the compressible cleansing matrix can engage one or more exterior surfaces of a needlefree connector when the capping and cleaning device is secured to the connector. The second (lower) opening of the inner housing is sized to allow the threaded valve portion of a needless connector to be capped and/or cleansed to be inserted into capping and cleansing device of the invention. The interior wall of the inner housing's central bore includes one or more thread-engaging tabs (or threads), preferably two (or more) oppositely disposed (or otherwise spaced) thread-engaging tabs, preferably near the lower opening. The thread-engaging tab(s)(or threads) is(are) configured to engage a complementary threaded region on the exterior surface of, for example, a needlefree connector such that the capping and cleansing device can, via association of the thread tabs or threads on the interior of the inner housing's central bore with complementary threads on the threaded portion of a needlefree connector, be securely threaded onto (or otherwise removably connected with) the targeted threaded portion of a needlefree connector for capping and, if desired, cleansing.

In some preferred embodiments, the outer surface of the inner housing includes an outer housing-retaining region that includes one or more structures, for example, a circumferential flange (or spaced flange elements), that allow the inner housing to be retained in the outer housing via association with one or more complementary structures (e.g., a circumferential flange (or spaced flange elements) or other suitable engaging elements) on the inner surface of the sidewall of the outer housing. Preferably, such configurations of complementary retaining elements also allow for smooth, low friction movement (i.e., rotation) of the inner and outer housings in relation to each other during certain operations, for example, during a disinfection procedure of a needlefree connector. In some of these embodiments, the retaining element(s) of the inner housing can mechanically engage an adjacent region on the inner surface of the sidewall of the outer housing, for example, when a user squeezes or otherwise applies sufficient force to the outer housing to deform it so as to allow engaging regions on the inner surface of the outer housing to engage corresponding engaging regions on the exterior surface of the inner housing so as to allow the inner and outer housings to rotate in unison (as would occur, for example, when a user attaches or removes a device from an NC). In some of these embodiments, the retaining element(s) of the inner housing can also serve as engaging elements with complementary regions, features, or structures on the inner surface of the sidewall of the outer housing adjacent or otherwise in close proximity thereto. In other embodiments, the outer surface of the inner housing further includes one or more outer housing engaging elements or regions designed to associate with one or more inner housing engaging elements or regions disposed on the interior or inner surface of the outer housing. Examples of such elements include, for example, a circumferential band of spaced teeth or teeth-like elements protruding from the exterior surface of the inner housing and positioned below the outer housing-retaining region (e.g., a circumferential flange), which teeth (or other suitable engaging structures) can be engaged by complementary structures arrayed on the interior surface of the outer housing when the housings are assembled into a functional subassembly.

In other preferred embodiments, the upper exterior surface of the inner housing includes an outer housing-engaging region that includes one or more structures that allow the inner housing to mechanically engage complementary structures (e.g., pawls or other suitable engaging elements) on the inner surface of the top of the outer housing so that when the complementary engaging elements of the outer housing and inner housing are brought into close proximity the engaging elements of the outer housing and inner housing engage, allowing the outer housing and inner housing to rotate in unison. Certain preferred embodiments of outer housing-engaging structures include spaced teeth (or other suitable engaging elements) arrayed on the top or upper surface of the inner housing's preferably cylindrical sidewall. As will be appreciated, when such inner and outer housing engaging elements are unmated or disengaged, a user can rotate or spin the outer housing in relation to the inner housing, as is, for example, done during a cleansing or disinfecting operation of the needlefree connector to which the device of the invention is attached. Thus, when the capping and cleansing device is secured to a needlefree connector, when such engaging elements are not functionally associated (or mated or otherwise engaged), a user can rotate the outer housing (and compressible cleansing matrix) in relation to the inner housing and connected needlefree connector. On the other hand, when the complementary elements on the inner surface of the top of the outer housing and the upper surface of the top of the inner housing are engaged (in whole or even partially), such as when a user applies downward pressure to the device to place it on or remove it from a needlefree connector, the inner and outer housings rotate together, allowing, for example, the capping and cleansing device to be attached to or removed from the NC.

In some preferred embodiments, the inner housing also includes an NC sealing member configured to provide a fluid tight seal between the capping and cleansing device of the invention and a needlefree connector connected thereto. In some embodiments the NC sealing member is an O-ring (or comparable seal) preferably disposed in a channel formed in the inner surface of the wall of the inner housing proximate to the second (lower) opening, typically below the thread-engaging tab(s)(or threads).

The devices of the invention also include an outer housing adapted or configured to retain the inner housing therein such that, when the device is attached to a needlefree connector, under certain conditions the outer housing can rotate (preferably about its central axis) in relation to the inner housing. Any suitable configuration of complementary mechanical or structural features or elements on facing or opposing surfaces can be used to provide retention of the inner housing inside the outer housing's main cavity and to allow for engagement and disengagement of the outer housing from the inner housing in order to allow the outer housing to be rotated in relation to the inner housing when the device is attached to a needlefree connector and a user desires to cleanse the corresponding surface(s) of the NC using the capping and cleansing device of the invention.

In some embodiments, when the device of the invention is attached to a needlefree connector, the inner and outer housings adopt a disengaged, neutral, or rotating configuration relative to each other such that a user can rotate the outer housing in relation to the inner housing to perform a cleansing operation on the valve portion of the NC to which the device is attached. Such a disengaged, neutral, or rotating configuration can be achieved by any suitable approach, including by providing complementary engaging elements or structures on adjacent surfaces of the inner and outer housings that under certain conditions, for example, when the outer housing is pulled up, pushed down, or squeezed by a user in relation to the inner housing, engage each other; otherwise the engaging elements remain disengaged, which allows rotation of the outer housing in relation to the inner housing when the device is secured to an NC. Features that allow transitioning between engaged and disengaged positions include springs or biasing or resilient elements or materials. In other embodiments, when the device is attached to a needlefree connector, the inner and outer housings adopt an engaged configuration relative to each other such that they rotate in unison unless a user applies sufficient force to the outer housing to cause the engaging elements to disengage and thus allow the outer housing to be rotated independently of the inner housing.

The outer housing includes a cylindrical cavity designed to receive and retain the inner housing using one or more features or elements that allow the outer housing to be rotated in relation to the inner housing if and when desired. The cavity is formed by a curved outer sidewall that in some embodiments is joined to a top portion of the housing about its periphery and which also preferably has a concentric central matrix well or matrix attachment region to or with which the compressible cleansing matrix is attached or otherwise associated, although in some embodiments some degree of eccentricity between the matrix well and central rotational axis of the outer housing may be desired. In some embodiments, the outer housing is formed by a sidewall that is tapered and/or has one or more steps.

In some preferred embodiments, the inner surface of the top of the outer housing includes one or more inner housing engaging elements or structures (e.g., teeth) designed to releasably engage complementary structures in the outer housing-engaging region on the top of the inner housing. Engagement of the outer housing's inner housing engaging structure(s) with those in the outer housing-engaging region of the inner housing allow a user to rotate the outer housing and inner housing in unison, for example, as a capping and cleansing device's inner housing is screwed onto the threaded portion of a needlefree connector to be cleansed and/or capped. Once the device is releasably secured to a needlefree connector via the inner housing, the outer housing's inner housing engaging elements or structure(s) can be (or are) disengaged from the outer housing-engaging elements of the inner housing, for example, by the biasing action or resilience of a the compressible cleansing matrix, thereby allowing a user to rotate the outer housing about its central axis in relation to the inner housing. A representative example of such engaging structures is shown in published US patent application publication no. 2018/0304067, although features such as an inner housing having an opening in its top to allow a compressible cleansing matrix attached to the inner surface of the top of the outer housing to extend into the bore of the inner housing so that it can contact surfaces of a needlefree connector upon connection of the former to the latter are also envisioned.

In some of these embodiments, the outer housing may include one or more vents to allow fluid and/or air from inside the device to escape as the capping and cleansing device is secured to a needlefree connector, while in other embodiments, no vent(s) is(are) provided. In embodiments with one or more vents, a membrane, filter, or other permeable or semi-permeable barrier may be employed to allow a unidirectional or bidirectional flow of air, gas, or vapor through the vent(s) but prevent the movement of microorganisms (e.g., bacteria, fungi, viruses, etc.) into the capping and cleansing device of the invention.

In certain preferred embodiments, the outer surface of the outer housing of a capping and cleansing device according to the invention includes one or more grip-enhancing structures (e.g., a plurality of vertical ridges) or coatings. Such grip-enhancing structures or coatings facilitate a user's grasp of the housing of a capping and cleansing device between her/his fingers, which can be helpful not only during insertion and removal of a needlefree connector from the capping cleansing device, but also during the cleansing process, where the user rotates the outer housing in relation to the inner housing in order to scrub and thereby clean or cleanse the surface(s) of the inserted needlefree connector with the compressible cleansing matrix of the device.

In some preferred embodiments, the devices of the invention include one or more elements or features arrayed on facing surfaces of the inner and outer housings that allow a user to sense that the outer housing is rotating in relation to the inner housing in order to provide cleansing action on the valve surface of the NC to which the device is attached. Such sensory feedback can include one or more of auditory, tactile, and/or visual stimuli generated from the device by rotation of the outer housing in relation to the inner housing.

In some of these embodiments, the devices of the invention comprise a resilient inner body disposed within a cap that can be rotated or turned in relation thereto when the capping and cleansing device is secured to a needlefree connector, and a compressible matrix element containing one or more antimicrobial reagents and having a structure to allow capped surfaces of the needlefree connector to be cleansed. More specifically, the resilient inner body has a wall that forms a central, interior (preferably cylindrical) bore that extends between oppositely disposed first and second (or upper and lower, respectively) openings. The interior wall of the central bore nearer the second (lower) opening includes one or more thread-engaging tabs (or threads), preferably two thread-engaging tabs disposed opposite to each other. The thread-engaging tab(s)(or threads) is(are) are configured to engage a complementary threaded region on the exterior surface of, for example, a needlefree medical valve. This allows the capping and cleansing device to be securely threaded onto the targeted threaded portion of a needlefree connector for cleansing and, if desired, capping that portion of the needlefree connector. The exterior surface of the resilient inner body includes one or more structures that allow it to mechanically engage and disengage complementary structures disposed on an inner surface of the cap.

In many embodiments, the resilient inner body's exterior surface includes a cap-engaging region that includes one or more structures such as spaced protrusions (e.g., teeth) that allow the resilient inner body to mechanically engage and disengage complementary engaging structures on an interior surface of the cap. Preferred embodiments of cap-engaging structures include alternating teeth and grooves (or channels) arrayed about the outer circumference of the resilient inner body, which teeth and grooves are complementary to one or more spaced engaging structures (e.g., teeth) disposed on the inner surface of the cap's outer wall. In other embodiments, the cap-engaging region of the resilient inner body is disposed on its inner surface for engagement with one or more complementary engaging structures (e.g., teeth) arrayed on the exterior or outer surface of matrix well wall. As will be appreciated, in configurations that include teeth and channels, the "teeth" can be raised protrusions and the "channels" can be the spaces or gaps between the raised protrusions.

The resilient inner body also includes a compressible region. In many preferred embodiments, it is located above the thread-engaging tab(s)(or threads) and cap-engaging region. The compressible region can be any structure that allows the resilient inner body to be compressed so as to bring the first and second openings closer together to allow disengagement of the engaging structures of the cap and resilient inner body. In preferred embodiments, the compressible region is a torsion spring, which in certain particularly preferred embodiments is a molded torsion spring formed from a plastic or other sufficiently flexible or resilient material, preferably during injection molding, as part of the resilient inner body.

In some embodiments, the resilient inner body is made from two or parts that are then assembled to form the complete inner body. For example, a resilient inner body can be formed as two or more separate parts that are assembled, one on top of the other, during manufacture of the capping and cleansing device of the invention. For instance, in embodiments where the resilient inner body is made of two parts, the upper part preferably comprises the compressible region (e.g., a torsion spring formed during injection molding of the upper part), while the lower part comprises the cap-engaging region and the thread-engaging tab(s)(or threads). In contrast, a representative three-part embodiment of a resilient inner body includes an upper section that comprises the first (upper) opening and the compressible region, a midsection that comprises the cap-engaging region, and a lower section that includes the thread-engaging tab(s) (or threads) and second (lower) opening. In an alternative three-part embodiment, the upper section comprises the first (upper) opening and cap-engaging region, the midsection comprises the compressible region, and the lower section includes the thread-engaging tab(s)(or threads) and second (lower) opening. As will be appreciated, the invention encompasses all possible combinations of parts having a cap-engaging region, compressible region, and a region to engage the threads of the threaded portion of a needlefree connector, with the proviso that the final combination be capable of being compressed to provide cap-engaging and -disengaging functionality such that when corresponding structures on the cap and inner body are engaged, the cap and inner body can rotate together about their central axes, and when the corresponding structures on the cap and inner body are disengaged by compression of the compressible region, a user can rotate the cap about its central axis in relation to, or independently from (i.e., the cap spins while the resilient inner body does not), the resilient inner body.

In embodiments of the invention where the resilient inner body is made from two or more parts, those parts, once assembled, preferably are mechanically connected such that they, too, move in unison, for example, when the capping and cleansing device of which they are a part is threaded onto the threaded portion of a needlefree connector, for example, a needlefree connector. Any suitable mechanical lock, and corresponding set of mechanical structures, can be used to link such parts together.

In some preferred embodiments, the inner housing or resilient inner body also includes a sealing member (i.e., seal) configured to provide a fluid tight seal between the capping and cleansing device of the invention and an NC connected thereto. The seal is preferably disposed in a channel formed in the inner surface of the wall of the resilient inner body proximate to the second (lower) opening, typically below the thread-engaging tab(s)(or threads).

Each device of the invention also includes a outer housing or cap in operable association with the inner housing such as a resilient inner body. A cap typically includes an outer cavity formed by a curved outer wall that is joined to a top portion, preferably about the top portion's periphery, and a preferably concentric central matrix well that extends from the top's inner surface into the outer cavity. The wall forming the matrix well is spaced from the cap's outer wall to form a resilient member housing that can be accessed through an opening created by the gap between the cap's wall and the matrix well wall. In many preferred embodiments, the inner surface of the cap's outer wall includes one or more engaging or locking structures (e.g., teeth) designed to releasably engage (i.e., corresponding structures can be engaged and disengaged, as desired) complementary structures in the cap-engaging region of the resilient inner body. In other embodiments, the cap's engaging or locking structure(s) is (are) disposed on the outer surface of the matrix well wall, which locking structure(s) is (are) designed to releasably engage complementary structures in the cap-engaging region on the inner wall of the resilient inner body. Engagement of cap's engaging or locking structure(s) with those in the cap-engaging region of the resilient inner body allows a user to rotate the cap and resilient inner body in unison, for example, as a capping and cleansing cap is screwed onto the threaded portion of a needlefree connector to be cleansed and/or capped. Once the device is releasably secured to a needlefree connector, the cap's locking structure(s) can be disengaged from those in the cap-engaging region of the resilient inner body, thereby allowing a user to rotate the cap about its central axis in relation to the resilient inner body. In some embodiments, the cap may include one or more vents to allow fluid and/or air from inside the device to escape as the capping and cleansing device is secured to a needlefree connector, while in other embodiments, no vent(s) is(are) provided.

The capping and cleansing devices of the invention also include a compressible cleansing matrix in the outer housing's matrix well. The compressible cleansing matrix can be, for example, an open-cell foam. The cleansing matrix is preferably secured to an inner surface of the outer housing so as to limit or restrict its rotation independent of the outer housing during outer housing rotation. The compressible cleansing matrix is configured to contact and cleanse one or more surfaces of a needlefree connector that contacts the matrix upon a needlefree connector's association with a capping and cleansing device of the invention. The compressible cleansing matrix attached to or otherwise associated with the outer housing can be axially compressed (i.e., compressed along the central axis of the outer housing's matrix well) upon insertion of a needlefree connector into a capping and cleansing device.

Because the needlefree connector surface(s) to be cleansed may be contaminated with microorganisms that form a biofilm (i.e., a matrix of microorganisms and extracellular material attached to a surface, which enables the microorganisms, typically bacteria and/or fungi, to adhere to a surface and carry out certain biochemical processes), the compressible cleansing matrix preferably has sufficient mechanical integrity when compressed to allow its use to disrupt any biofilm that may be present on a surface of the needlefree connector that is contacted by the cleansing matrix. Disruption of biofilm can occur by rotating, twisting, or otherwise moving a then-compressed cleansing matrix in relation to the needlefree connector (e.g., a needlefree medical valve), for example, by rotating the outer housing (to which the compressible cleansing matrix is attached or otherwise associated or retained) in relation to the inner housing (e.g., a resilient inner body) of the capping and cleansing device and the needlefree connector to which inner housing is releasably attached. The resulting friction between the compressed cleansing matrix and surface of the needlefree connector disrupts the biofilm, thereby cleansing, and preferably sterilizing, the needlefree connector. Leaving the capping and cleansing device secured to (i.e., capping) the needlefree connector after such cleansing will limit, and preferably preclude, biofilm regrowth and/or the microbial recolonization of cleansed surfaces (which remain in contact with the compressible cleansing matrix) of the needlefree connector.

In preferred embodiments, the compressible cleansing matrix includes one or more cleansing reagent species dispersed therein, preferably at the time the device is manufactured, although in some embodiments, the cleansing reagent may be dispersed into the matrix just prior to the matrix coming into contact with a needlefree connector. In embodiments of the latter sort, the cleansing reagent is preferably housed in the body of the capping and cleansing device in a reservoir configured to rupture upon association of a needlefree connector for cleansing. Such a reservoir can be disposed between the matrix and needlefree connector, or, more preferably, between the rotatable cap and compressible cleansing matrix. Preferred cleansing reagents include antimicrobial reagents such as isopropyl alcohol, chlorhexidine, and silver ions. In some embodiments, the capping and cleansing device of the invention will include a valve or opening to allow liquid in the cleansing reagent to evaporate.

In some preferred embodiments, the compressible cleansing matrix is comprised of two or more components. In some of such embodiments, one portion of the matrix is attached to the inner surface of the outer housing and another portion is secured to the inner surface of the wall forming the matrix well. If present, the portion of the compressible cleansing matrix secured to the inner surface of the matrix well wall is preferably configured to radially compress upon association with a needlefree connector to be capped and cleansed. When a cleansing matrix is comprised of two or more components, the matrix components may be made from the same of different material(s).

As described, the central matrix well is adapted to receive the compressible cleansing matrix. The surface(s) of the central matrix well in contact with the matrix preferably includes one or more retaining structures to retain the compressible cleansing matrix so as to link its rotation or movement to that of the cap, particularly when the engaging structures of the cap and resilient inner body are disengaged so as to allow cap rotation during a needlefree connector cleansing procedure. Such retaining structures include ridges and other protrusions from the surface of central matrix well in contact with the compressible cleansing matrix. An adhesive can also be used to adhere that portion of the compressible cleansing matrix to a desired position in the matrix well.

In various embodiments, the outer surface of the outer housing of a capping and cleansing device according to the invention includes one or more grip-enhancing structures or coatings, e.g., a plurality of vertical ridges. Such grip-enhancing structures or coatings facilitate a user's grasp of the body of a capping and cleansing device between her/his fingers, which can be helpful not only during insertion and removal of a needlefree connector from the capping cleansing device, but also during the cleansing process, where the user rotates the outer housing in relation to the inner housing in order to scrub and thereby clean/cleanse the surface(s) of the inserted needlefree connector with the compressible cleansing matrix.

The inner and outer housings can be made from any suitable material or combinations of different materials. Plastics are particularly preferred. The material(s) used to manufacture the outer housing may be the same or different as the material(s) used to produce the inner housing.

The outer housing and its various components are preferably formed as a single, integral unit during manufacturing (e.g., by injection molding). The inner and outer housings can be manufactured by any suitable process, including extrusion, injection molding, and additive manufacturing (e.g., 3D printing). After manufacturing, an inner housing is inserted into an outer housing to form a capping and cleansing device of the invention. For securing the inner and outer housings together as a functional subassembly that can transition between engaged and disengaged configurations to provide for unitary or independent rotation of the outer housing in relation to the inner housing, any suitable retaining structure, or group of structures, that provides for movement, i.e., rotation, of the outer housing in relation to the inner housing can be used. Such structures include attachment mechanisms such as "snap-fit" mechanisms where interacting parts are sufficiently flexible and have preferably have tapered surfaces so facilitate assembly.

A compressible cleansing matrix can be positioned in the matrix well before of after an inner housing and outer housing are operably associated. In preferred embodiments, a suitable adhesive is used to securely adhere the compressible cleansing matrix, or, if the matrix comprises two or more parts, its various portions, to one or more inner surfaces of the outer housing's matrix well. In some embodiments, the surface of the matrix well that contacts the compressible matrix includes a structure to assist in securely retaining the matrix in the well, thus ensuring that it moves in conjunction with the cap when the outer housing is rotated during a cleansing procedure.

In preferred embodiments, the capping and cleansing devices include a removable lid or seal attached to the outer housing to seal the device, thus separating the interior spaces and structures of the device from the external environment. Such a lid or seal prevents exposure of the devices's interior, including the inner housing and compressible cleansing matrix, to the environment until the seal is removed, typically by a healthcare worker just prior to her/his use of the capping and cleansing device to cap and then, if desired, to clean/cleanse the needlefree connector (e.g., needlefree medical valve) to which it is connected. In preferred embodiments, such cleansing substantially disrupts any biofilm that may exist on surfaces contacted by the compressible cleansing matrix. If desired, the capping and cleansing device can be left in place (typically after cleansing the needlefree connector attached thereto) in order to cap the needlefree connector until it is further accessed, thereby minimizing exposure of capped exterior surfaces of the connector to potential pathogen contamination (and biofilm formation) from the surrounding environment. Seals are typically installed during manufacture of a capping and cleansing device of the invention. In those embodiments where the capping and cleansing devices are sterilized during manufacture (e.g., by irradiation, exposure to ethylene oxide, etc.), seals are preferably applied prior to sterilization.

Other aspects of the invention concern methods of cleansing and/or capping needlefree connectors using a capping and cleansing device according to the invention. Such methods typically involve transitioning the inner and outer housings from an engaged to a disengaged configuration after the device has been connected to a needlefree connector as to allow the outer housing to spin or rotate in relation to the inner housing. Such compression facilitates contact between the device's compressible cleansing matrix and the associated surface(s) of the needlefree connector. Spinning or rotation of the outer housing in relation to the inner housing, and the associated surface(s) of the needlefree connector, allow those surfaces to be scrubbed, thereby cleansing them. Preferably, such cleansing methods provide for the disruption of any biofilm present on the surface(s) of the needlefree connector associated the capping and cleansing device. And in those embodiments where the compressible cleansing matrix contains one or more antimicrobial reagents, microbes and pathogens present in such biofilm and/on on such surface(s) are destroyed or rendered nonviable.

Herein, the compressible cleansing matrix of a capping and cleansing device of the invention comprises one or more cleansing reagent species dispersed in a substrate. The cleansing matrix substrate can be any substance that can conform, mold, or compress in a manner that enables the effective friction-based cleansing of the site or portion of the needlefree connector to be cleansed, including the top surface of the site, side surface, and any threads or grooves, if present, and provide the cleansing reagent at least at a surface level. Examples of the compressible cleansing matrix include cotton, open or closed cell foam such as polyethylene foam, or other substance that can hold or carry the cleansing reagent.

In some embodiments, the cleansing reagent species is(are) dispersed in or otherwise combined with the compressible cleansing matrix during the process used to manufacture the capping and cleansing device, while in other embodiments, the device is configured such that the cleansing reagent(s) is(are) released for dispersion into the compressible cleansing matrix post-manufacture, but when or prior to the time the matrix is brought into contact with the needlefree connector to be cleansed. The cleansing reagent can be any chemical, substance, or material that cleans the site of bacterial or even viral microorganisms, biofilm, etc., or any carrier that contains such chemical, substance or material. Examples of cleansing reagents include isopropyl alcohol, chlorhexidine, chlorhexidine digluconate, povidone-iodine, hydrogen peroxide, soap, and hydrochloric acid, silver ions and salts (e.g., silver acetate, silver lactate, silver nitrate, etc.), etc.

In accordance with the invention, a cleansing reagent comprises an active ingredient capable of cleansing a surface of a needlefree connector. Any active ingredient that can be used effectively to rapidly cleanse a medical fitting or medical line connector (e.g., a needlefree connector) can be adapted for use in practicing the invention, and are generally classified as antibacterial and/or antifungal reagents, antiseptic or antimicrobial reagents, wide spectrum disinfectants, and/or parasiticides, as well as combinations of such reagents. Particularly preferred are biocompatible cleansing reagents, as the devices of the invention are intended for human and/or veterinary use, including alcohols, antibiotics, oxidizing reagents, and metal salts. Representative examples of such active ingredients include bleach, chlorhexidine, ethanol, isopropyl alcohol, hydrogen peroxide, sodium hydroxide, and an iodophor dissolved or otherwise dispersed in a suitable solution, suspension, or emulsion. Other active ingredients having suitable cleansing effects can also be used. These include alcohols (e.g., ethanol, benzyl alcohol, isopropyl alcohol, phenoxyethanol, phenethyl alcohol, etc.); antibiotics (e.g., aminoglycosides, such as amikacin, apramycin, gentamicin, kanamycin, neomycin, netilmicin, paromomycin, rhodostreptomycin, streptomycin, and tobramycin; bacitracin; chloramphenicol; erythromycin; minocycline/rifampin; tetracycline; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; etc.), quaternary ammonium chlorides; quaternary ammonium carbonates; benzalkonium chloride; chlorinated phenols; fatty acid monoesters of glycerin and propylene glycol; iodine; iodine containing compounds, such as 3-iodo-2-propynyl butyl carbamate (IPBC); iodophors, such as povidone-iodine (Betadine 100%, which contains providine iodine as the active ingredient); hydantoins, such as dimethylhydantoin and halogenated hydantoins; isothiazolinones; parabens, such as methylparaben, ethylparaben, and propylparaben; chloroxylenol; chlorhexidine and its salts; chlorhexidine/silver-sulfadiazine; chlorhexidine acetate; chlorhexidine gluconate (e.g., Hibiclens); chlorhexidine hydrochloride; chlorhexidine sulfate; benzoic acid and salts thereof; benzalkonium chloride; benzethonium chloride; methylbenzethonium chloride; chlorobutanol; sorbic acid and salts thereof; imidazole antifungals (e.g., miconazole); butocouazole nitrate; mafenide acetate; nitrofurazone; nitromersol; triclocarban; phenylmercuric nitrate or acetate (0.002%); chlorocresol; chlorbutol; clindamycin; CAE (Anjinomoto Co., Inc., containing DL-pyrrolidone carboxylic acid salt of L-cocoyl arginine ethyl ester); cetylpyridinium chloride (CPC) at 0.2%, 0.02%, and 0.002% concentrations; 9.8% isopropyl alcohol; 1% ZnEDTA; mupirocin; and polymyxin (polymyxin b sulfate-bacitracin). Additionally, other useful compounds and compositions include Miconazole, Econazole, Ketoconazole, Oxiconizole, Haloprogin, Clotrimazole, butenafine HCl, Naftifine, Rifampicin, Terbinafine, Ciclopirox, Tolnaftate, Lindane, Lamisil, Fluconazole, Amphotericin B, Ciprofloxecin, Octenidine, Triclosan (2,4,4'-trichloro-2'-hydroxydiphenyl ether), Microban (5-chloro-2phenol (2,4 dichlorophenoxy). Useful metals include silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine. Cleansing reagents are often compositions that comprise the desired active ingredient(s) in admixture with other ingredients, such as carriers and liquid solvents.

The particular active ingredient(s) selected as a cleansing reagent for a given application will be compatible with the compressible cleansing matrix and material(s) used to form the outer housing, inner housing, and other components of the particular device. In some embodiments, the cleansing reagent is dispersed in the compressible cleansing matrix after the matrix is formed. For example, a cleansing reagent can be dispersed by saturating or supersaturating a compressible cleansing matrix during manufacture of the device, preferably before it is sealed. In other embodiments, the cleansing reagent can be dispersed during the process used to manufacture the compressible cleansing matrix. As will be appreciated, the materials used to prepare the cleansing reagent should be compatible with the constituent or constituents that comprise the compressible cleansing matrix such that the substrate does not appreciably degrade or otherwise suffer loss of structural integrity prior to being used to cleanse a needlefree connector (e.g., a needlefree medical valve). Similarly, the cleansing reagent should be biocompatible, such that it will not harm a patient in the event of contact or should some amount of the cleansing reagent be admitted into the fluid-carrying portion of a needlefree medical valve, as well as with materials used to form needlefree medical valves (or other needlefree connector).

In preferred embodiments, the material used to form the compressible cleansing matrix is any suitable absorbent, compliant, pliable, resilient, fibrous, or porous material, or combination of materials, than can be wetted and/or impregnated with a cleansing reagent and which can easily and readily adapt to complex surface contours (e.g., luer threads, concave and convex surfaces, flanges, etc.) likely to be engaged upon contact with, for example, a needlefree medical valve to be cleansed. Such materials include those that are synthetic or naturally occurring, and they may be of homogeneous or heterogeneous composition. Preferred synthetic materials include fibrous, foam (e.g., a felted foam), and gel compositions, particularly those having directionally oriented natural or synthetic fibers, or combinations thereof. Preferred naturally occurring materials useful as substrates include fibrous naturally occurring materials, including plant-derived materials such as cotton and paper products, as well as animal-based fiber products such as wool. Other preferred natural materials are sponges.

As will be appreciated, in order to achieve the desired cleansing effect, a compressible cleansing matrix, or the component part(s) thereof designed to contact a needlefree connector such as a needlefree medical valve, preferably are made of a material (or combination of materials) that allow the cleansing element to thoroughly cleanse surfaces of needlefree connectors such as needlefree valves or luer access devices, particularly those surfaces that are exposed to air and thus are at risk for contamination with infectious or pathogenic reagents, and biofilms containing the same, and are also intended to form part of the fluid flow path for fluids to be introduced into a patient, for example, IV solutions, medications, blood and blood products, etc.

Preferably, the material used to produce the compressible cleansing matrix should be sufficiently compliant to allow the compressible cleansing matrix to deform under the pressures experienced during normal use in order to allow it to conform to the external structures present on the surface(s) of the needlefree connector to be cleansed. This assures intimate, cleansing contact between the compressible cleansing matrix and at least those exposed surfaces of, for instance, a needlefree connector designed to come into contact with fluid entering the valve, such as IV fluids. In addition, the compressible cleansing matrix preferably allows for the retention of a liquid cleansing reagent, for example, in capillary spaces, in the void volume of foams, sponges, etc. The compressible cleansing matrix may also be engineered such that it includes cleansing reagents such as silver ions and/or other suitable materials.

Preferred natural materials from which compressible cleansing matrices can be formed include those derived from cotton and naturally occurring sponges. As those in the art appreciate, processed cotton fibers are composed almost entirely of the natural polymer cellulose. In such fibers, 20-30 layers of cellulose are coiled into a series of spring configurations, which makes the fibers absorbent and gives them a high degree of durability and strength. For example, woven cotton sheets, as are often used in the manufacture of sterile cleansing pads that are then saturated with a 70% isopropyl alcohol (IPA) solution, can be used as substrates for cleansing elements according to the invention. Any suitable configuration may be used. For example, a woven cotton sheet can be cut into numerous similarly sized pieces, each of which can be used as a substrate. In many embodiments, after attachment to the inside surface of a layer of the container (e.g., through the use of an adhesive, double-sided, tape, etc.), the matrix is ready for the addition of a suitable cleansing reagent. Alternatively, cotton fibers can be spun onto the inside surface of the cap. Other fibers, be they naturally occurring, synthetic, or combinations of natural and synthetic materials, having similar properties can also readily be adapted for use as compressible cleansing matrices.

Another class of materials for compressible cleansing matrix fabrication is directionally oriented fibrous materials. These include, without limitation, materials comprised of cellulose fibers, glass fibers, and polyester fibers, as well as materials comprised of combinations of two of more of these and/or other materials. Such bonded synthetic fibers use capillary action to precisely absorb, retain, transfer, and/or release liquids or vapor in desired amounts. A broad range of synthetic polymers can be used to form the fibers, and, if desired, they may be treated for functional purposes, for example, to contain a cleansing reagent dispersed therein, to provide a vapor barrier or other coating over a portion of the product's surface, etc. The geometric shape of these materials can also be customized for particular applications, thereby permitting easy integration into substrate configurations having the desired device thickness, widths, length, diameter, etc.

Other representative classes of materials suitable for use as compressible cleansing matrices include gel-forming polymers and foams such as agarose, agar, polyacrylamide, and other synthetic porous materials that can be formed into layers, sheets, columns, or other shapes compatible with practicing the invention. Representative gelatinous materials include hydrogels (i.e., cross-linked polymers that absorb and hold water), particularly those made from agarose, (2-hydroxyethyl)methacrylate and its derivatives, and synthetic carbohydrate acrylamides.

Still other classes of materials include porous polymer sponges. Such sponges can be formed from any suitable material, including polyethylene, polypropylene, olytetrafluoroethylene, polyvinylidine difluoride, polynitrile, and polystyrene. Many such porous polymer sponges are commercially available in a wide variety of shapes, pore density and size, etc. Additionally, polymer sponges can be made by polymerizing appropriate monomers according to conventional foam forming techniques. In general, sponges have an open pore structure to allow movement of a solvent such as a liquid cleansing reagent. The sponge surface should include open pores to provide entry of liquid cleansing reagents (e.g., alcohol, iodine-containing solutions, etc.), and, as with other materials used to form matrices, the particular material chosen is preferably inert, i.e., not reactive with components of the cleansing reagent, the body of the capping and cleansing device, or the materials used to produce needlefree connectors such as needlefree medical valves.

Surgical foams are another preferred class of materials that can be used to make compressible cleansing matrices. The materials can be natural or synthetic, as desired. Suitable foams include rubber latex, polyurethane, polyethylene and vinyl foams. Preferably, such foams are made from any suitable biocompatible polymer, for example, polyvinyl alcohol (PVA) or polyurethane. One preferred foam material is Microbisan™, a hydrophilic polyurethane foam that is impregnated with silver ions (Lendell Manufacturing, St Charles, Mich.). Preferably, such foams are highly absorbent and thus suitable for use with liquid cleansing reagents. In other embodiments, the material used to form the foam is well-suited for dispersion of a dry cleansing reagent, such as silver ions. Again, it is preferred that foam materials, if used to as a substrate, be inert. Also, they are preferably sufficiently flexible to conform to the variety of different shapes and surface configurations (e.g., double seal fluid access points, luer threads, etc.) encountered in the field given the multitude of medical valve shapes, sizes, and configurations. In this way sufficient contact between the cleansing surface(s) of the capping and cleansing device and the surface(s) of the needlefree connector to be cleansed can be ensured. Another advantage of some synthetic foams (as well as certain other polymeric materials from which substrates may be formed) is that they can easily be injected in a desired volume into a shell or housing during manufacture, after which they expand to assume the desired substrate size, density, porosity, etc.

Furthermore, compressible cleansing matrices can include chemicals to indicate a functional change therein, for example, by using a color change to signal a change from a wet to a dry state, or, alternatively, that the matrix material has been properly wetted with a liquid cleansing reagent dispersed into the substrate by a health care worker just prior to use, as opposed to during manufacture of the device. Thus, depending on the system used, a color change in the matrix could be used to indicate that the cleansing reagent in the compressible cleansing matrix has evaporated prior to use and thus the particular cleansing device should not be used, perhaps due to a leak in the capping and cleansing device's storage container. Alternatively, when, for example, a colored liquid cleansing reagent is used, the user can visually confirm dispersion of the reagent in the matrix by assessing whether the colored cleansing reagent is dispersed throughout the matrix. When colored cleansing reagents are used, it is preferred that the material(s) use to make the resilient inner body and/or cap of the capping and cleansing device be clear or translucent, or include one or more clear or translucent windows, in order to allow easy visualization of any color change prior to or during use of the capping and cleansing device.

Capping and cleansing devices of the invention and their constituent parts (e.g., the resilient inner body, cap, compressible cleansing matrix, sealing ring, seal, etc.) can be made from any suitable material(s) and assembled using any suitable process.

Preferably, the outer surface of a capping and cleansing device's outer housing intended for grasping by a user has a non-slip surface, i.e., one having a high coefficient of friction so that when the outer portion of a capping and cleansing device is held in a user's fingers and positioned to cleanse a needlefree connector so that the outer housing can be rotated in relation to the inner housing and needlefree connector with minimal or no slippage between the device and the user's fingers (gloved or ungloved). Examples of such non-slip (or high friction) surfaces include those having ridges, valleys, dimples, bumps, or other features designed to enhance friction, as well as combinations of two or more of such features. Such features can be introduced into a device's outer surface(s) as part of the manufacturing process. Alternatively, a non-slip coating can be applied to one or more of the outer surfaces of the outer housing.

In general, the capping and cleansing devices of the invention are provided to users in a sealed, sterile manner. If desired, labeling information, logos, artwork, manufacturing, and/or regulatory data (e.g., lot number, expiration or "use by" dates, etc.) may also be printed or otherwise applied to individual capping and cleansing devices. In addition, information such as a bar code (to allow use of the device to tracked, for example) may also be included on individual capping and cleansing devices.

As will be appreciated, cleansing devices may be packaged individually or in groups of two or more units as kits, which can further include instructions for use of the capping and cleansing device(s), as well as other information, logos, artwork, manufacturing, and/or regulatory data.

In preferred embodiments, packaged capping and cleansing devices are sterilized using a suitable process, such as irradiation. In a particularly preferred practice, the capping and cleansing device s of the invention are sterilized as part of the manufacturing process. Here, "sterilization" refers to any process that effectively kills or eliminates transmissible reagents, e.g., bacteria, viruses, fungi, prions, spores, etc. that may be present in any component of a device according to the invention. In preferred embodiments, sterilization can be achieved by heating, chemical treatment, irradiation, and other processes. Indeed, any sterilization process compatible with the materials used to make the capping and cleansing device can be employed. A particularly preferred sterilization process is an irradiation process. Such processes include irradiation with x-rays, gamma rays, or subatomic particles (e.g., an electron beam). In general, when a sterilization process is used in the context of the invention, the process is employed on a cleansing article after it has been sealed and/or packaged. Chemical sterilization processes can also be used, for example, sterilization using ethylene oxide (EtO).

The invention also concerns methods of using the instant single-use capping and cleansing devices of the invention. Such methods include using the devices to cleanse and, if desired, cap needlefree connectors such as needlefree connectors, luer access devices, and the like. To perform such methods, the portion of a needlefree connector to be cleansed is threaded into the central bore of the inner housing of a capping and cleansing device, typically after the user (e.g., a nurse) removes a seal that spans the opening in the device. Such insertion brings the site of the needlefree connector into contact with (i.e., brought into cleansing association with) the compressible cleansing matrix portion(s) of the device. In preferred practice, once the compressible cleansing matrix is in contact with the surface(s) of the needlefree connector to be cleansed, the outer housing automatically disengages the engaging elements in the inner and outer housings to allow rotation of the outer housing in relation to the inner housing and needlefree connector previously releasably connected to capping and cleansing device. Such contact and cleansing action can be for any desired period, with periods of about one second to about ten to twenty seconds being particularly preferred.

After cleansing, the needlefree connector can be removed from the capping and cleansing device, after which the capping and cleansing device may be discarded. Alternatively, after cleansing, the capping and cleansing device can be left attached to the needlefree connector, capping a portion thereof until such time as access to the needlefree connector is desired, capping it and protecting it from contamination. At that time, the capping and cleansing device can be removed and discarded. If desired, just prior to removal, a cleansing process can be repeated.

After removal of a capping and cleansing device from a cleansed needlefree connector, a fluid-containing medical reservoir (e.g., a syringe containing a medication, an IV bag, etc.) may be immediately connected to the cleansed needlefree connector. In preferred embodiments where the cleansing reagent is a solution, the surface(s) of the needlefree connector is preferably allowed to dry (or is(are) dried, for example, by wiping with a sterile, absorbent cloth or wipe, which cloth or wipe may be dry or wetted with a volatile, compatible solution such as 70-100% alcohol) prior to connecting the needlefree connector to a fluid reservoir. In preferred practice, such cleansing methods result in at least a 2-fold, 5-fold, or 10-fold or more reduction in microorganism contamination on the accessible surface(s) that have been cleansed. Even more preferably, the level of reduction may exceed a 100-fold, a $10^3$-fold, a $10^4$-fold, a $10^5$-fold, a $10^6$-fold, or $10^7$-fold reduction in microorganism contamination on the accessible fitting surface.

In addition to methods for cleansing accessible surfaces of luer access devices and the like, the devices of the invention provide methods of reducing infection risk in a patient connected to devices, such as a peripheral IV line, a central IV line, or a peripherally inserted central catheter, configured for delivering fluids directly into the patient's blood stream. The risk reduction afforded by the devices of the invention may vary depending upon many factors, such as patient age and condition, the condition being treated, the location where medical services are being delivered, patient density, the level of contaminating microorganisms in the environment, the quality of air handling equipment in the medical facility, the degree of training of medical personnel charged with cleansing the access device, the method(s) used to periodically cleanse the medical fitting, intervals between cleansing procedures, the particular configuration of the capping and cleansing device, the particular configuration of the needlefree connector, whether the capping and cleansing device is left on the cleansed site of the needlefree connector in order to provide capping, etc. Risk reduction can be established using any suitable method, for example, by assessing HAI frequency in the presence and absence of using cleansing devices according to the invention. Reductions of HAI infection risk of 1-100% or more, including up to 1000% or more, are envisioned through use of capping and cleansing devices according to the invention. As will be appreciated, reductions in infection risk (e.g., HAI risk) will translate to improved patient outcomes (through reduced morbidity and mortality) and reduced expenditure on treating HAI's.

REPRESENTATIVE EMBODIMENTS

To further illustrate and describe certain preferred, representative embodiments of the invention, the reader is directed to the appended drawings, FIGS. 1-10, which illustrate various particularly preferred embodiments of the capping and cleansing devices of invention. A description of these preferred, representative embodiments follows.

FIG. 1 shows several drawings ((a)-(h)) of a representative capping and cleansing device of the invention (10), its constituent parts (views (b)-(h)), and the device associated with a needlefree connector (view (a)). The constituent parts include a cap having a cap portion (11) adapted to receive and retain the compressible cleansing matrix (80) and a resilient inner body (30) associated with the cap portion (11) and adapted to engage one or more complementary features of the cap portion so as to prevent the cap portion and resilient inner body from moving independently of each other under certain conditions while under other conditions allowing the cap portion (11) and to move independently of each other. For example, after attaching the device (10) to a needlefree connector (100) (producing a capped needlefree connector (200)), a user an compress the resilient inner body (30) of the device (10) by applying pressure to compress the cap (10) against the needlefree connector (100) so as to allow the cap (10) to be rotated in relation to the resilient inner body (30) and the needlefree connector (100). Such action brings the compressible cleansing matrix (80) and surface(s) of the needlefree connector (100) desired to be cleaned, for example, the valve surface of a needlefree medical valve, into contact, and rotation of the cap (10) in relation to the needlefree connector (100) creates friction that can disrupt, for example, biofilm that may be present on the needlefree medical valve's valve surface, which surface can be in the fluid path of fluids moving through the medical valve.

Figure 2B:
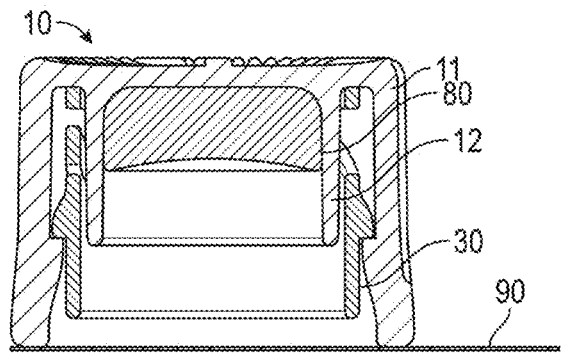

FIG. 2(a) is an exploded view of a representative capping and cleansing device of the invention (10) and a needlefree connector (100). Visible are the cap (10), including its cap portion (11) into which the compressible cleansing matrix (80) and resilient inner body (30) are positioned, and a luer-based needlefree connector (100) that is a needlefree medical valve, the male end (105) of which has a collar (101) and threads (102) for connecting the valve to a female threaded portion of a complementary luer fitting of another needlefree connector (not shown). View (b) is a cross-section side view of the cap (10) shown in view (a) while it was still sealed with a seal (90). As shown, the cap portion (11), compressible cleansing matrix (80), and resilient inner body (30) are operably assembled. The compressible cleansing matrix (80) is preferably positioned in a matrix well (12) formed into and protruding from the inner surface of the cap portion (11). The height of the matrix well (12) should allow retention of the compressible cleansing matrix (80), and in some embodiments it can be sized to act as a stop that can bear against the collar of a needlefree connector (100) to which the cap is attached when the cap is compressed by a user and rotated to cleanse desired surfaces of the needlefree connector (100).

Figure 2C:
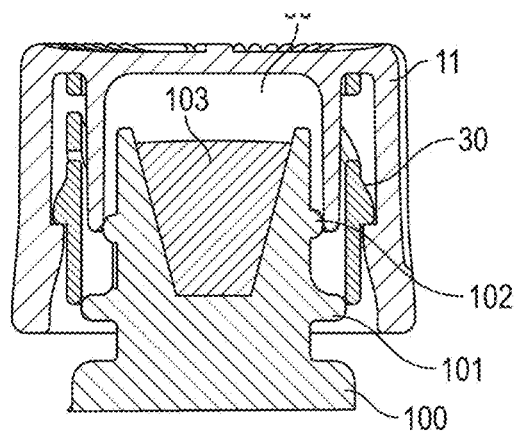
Figure 2D:
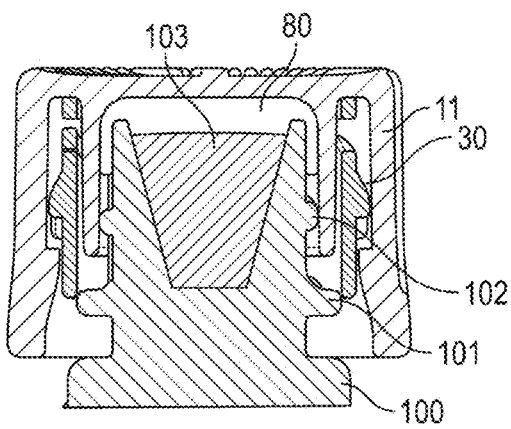
Figure 3A:
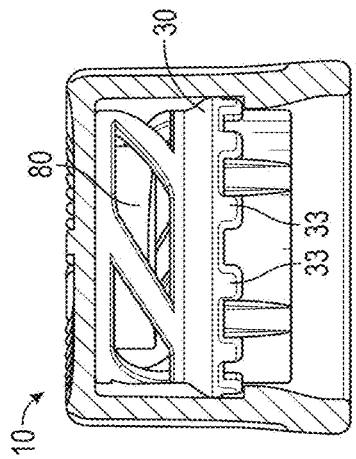
FIG. 3A-FIG. 3F shows six different views of a representative capping and cleansing device of the invention. Views (a)-(c) show the device in a static position, where the cap and resilient inner body are engaged such that the cap, and hence the compressible cleansing matrix associated therewith, cannot rotate in relation to the device's resilient inner body. Views (d)-(f) show the same representative device with the cap and resilient inner body in movable relation such that the cap (and the compressible cleansing matrix associated therewith) can be rotated in relation to the device's resilient inner body.
Figure 3B:
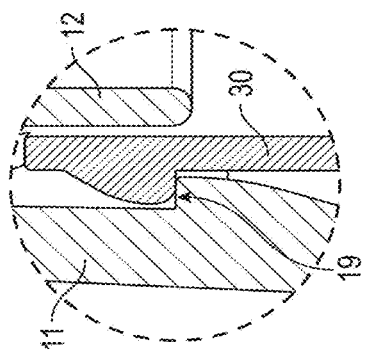
Figure 3C:
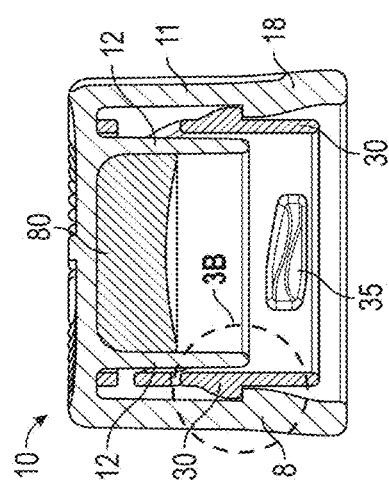
Figure 3D:
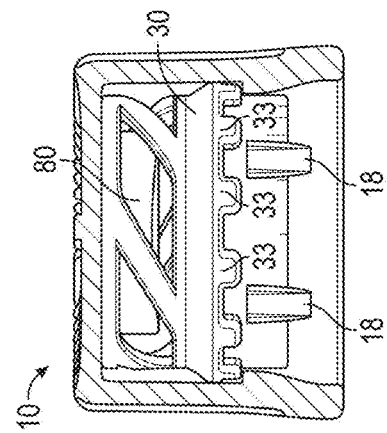
Figure 3E:
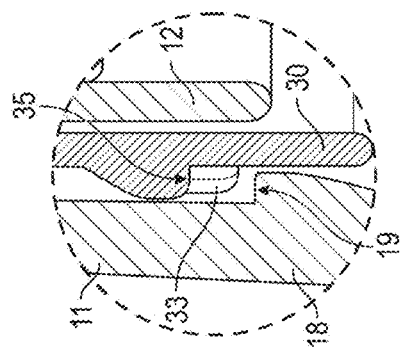
Figure 3F:
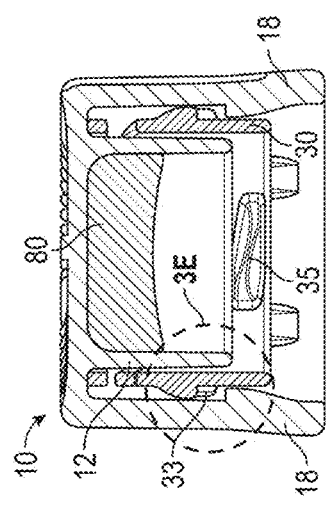

Views (c) and (d) of FIG. 2 show the cap (10) threaded onto the medical valve (100) in capping and cleansing configurations (views (c) and (d), respectively). As shown in these views, the compressible cleansing matrix (80) of the cap (10) bears against the valve surface of the valve stem portion (103) of the medical valve (100). In the capping view, view (c), the cap (and compressible cleansing matrix (80)) is not compressed. The diameter of the matrix well (12) allows the cap to slide over the threads (102) of the medical valve (100) when the cap is pushed toward the medical valve (100) by user wishing to cleanse the surface of the valve stem portion (103). View (d) shows the cap (10) compressed against the medical valve (100). User-induced compression results in the cap portion (11) moving closer to the body of the medical valve (100) by virtue of compression of the resilient inner body (30) and compressible cleansing matrix (80). This motion also results in disengagement of the complementary mechanical retaining elements of the cap portion (11) and resilient inner body (30), thus allowing the user to rotate cap portion (11) and the compressible cleansing matrix (80) of the cap in relation to the valve surface, thereby allowing cleansing of that surface.

FIG. 3 shows six different views of a representative capping and cleansing device of the invention. Views (a)-(c) show the device (10) in a static, non-compressed, non-rotable position, where the cap portion (11) and resilient inner body (30) are engaged such that the cap (10), and hence the compressible cleansing matrix (80) associated therewith, cannot rotate in relation to the device's resilient inner body (30). Views (d)-(f) show the same representative device (10) with the cap portion (11) and resilient inner body (30) in movable relation such that the cap portion ((11), and the compressible cleansing matrix (80) associated therewith) can be rotated in relation to the device's resilient inner body (30). The inner surface of the resilient inner body (30) includes one or more (preferably two) tabs (35) to engage the threads of a needlefree connector (100). In the embodiments shown in the Figures, the outer surface of the resilient inner body (30) includes a plurality of teeth (33) or other structures spaced about the resilient inner body's outer circumference designed to engage complementary spaced structures (e.g., ribs (18)) spaced on the inner surface of the cap portion (11). When the cap (10) is uncompressed, the teeth (33) engage the ribs (18) and effectively lock the cap portion (11) and resilient inner body (30) together so that they rotate together. This enables the cap (10) to be threaded, for example, onto a complementary luer fitting of a needlefree connector using the tabs (35) on the inner surface of the resilient inner body (30) in order to provide a capping function (to remove the cap from the needlefree connector, the process is reversed). To provide cleansing action, once secured to the needlefree connector, the cap (10) can then be compressed by a user, which pushes the cap portion (11) toward the needlefree connector's fitting and compresses the compressible cleansing matrix (80) against the surface(s) of the connector (100) to be cleansed.

Figure 4:
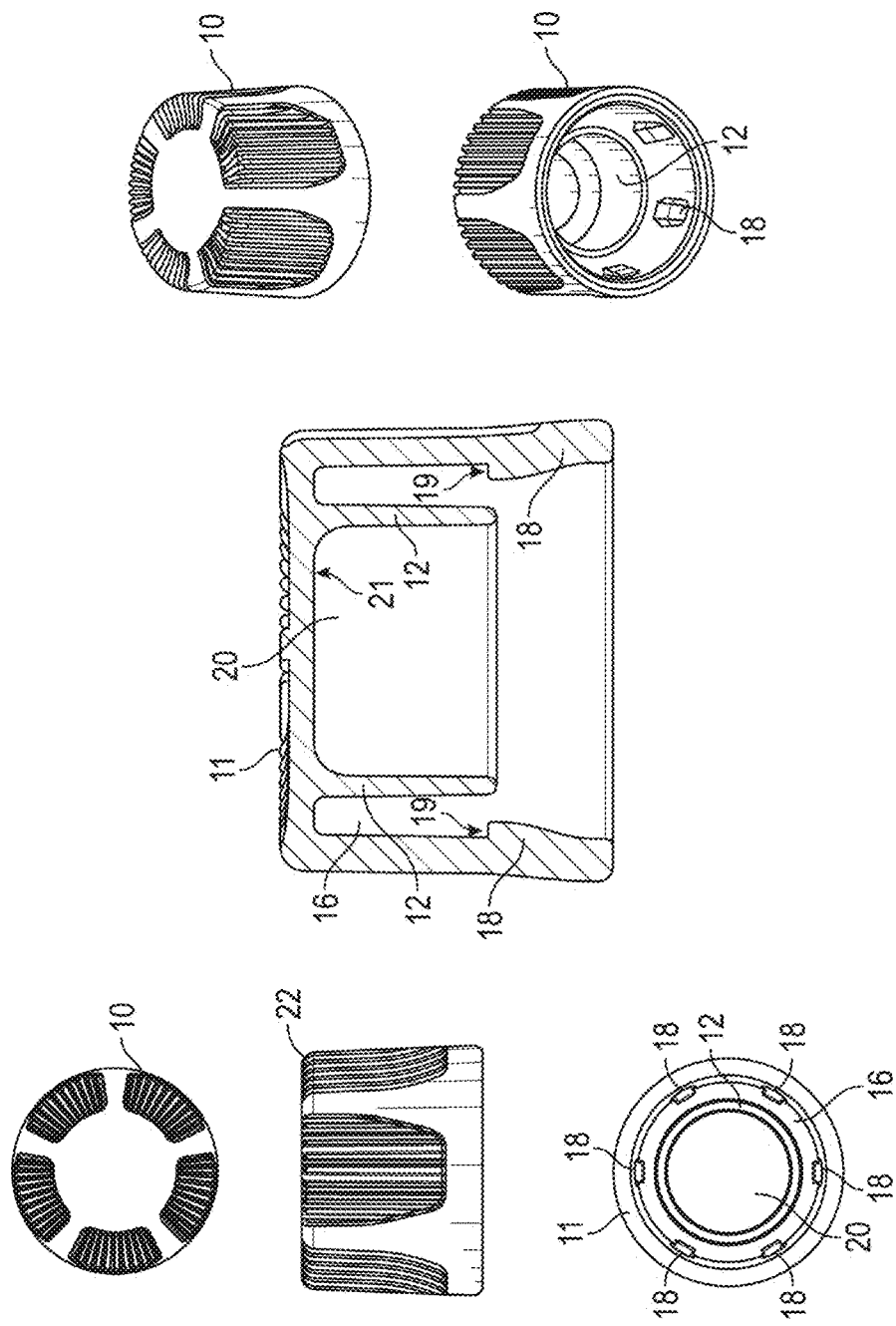
FIG. 4 shows views of the cap portion of a representative capping and cleansing device of the invention. View (a) shows a top view of the cap portion. View (b) shows a side view of the cap portion. View (c) shows a bottom view of the cap portion. View (d) shows a cross-sectional view of the cap portion. Representative measurements of this particular embodiment are shown on views (b) and (d).
Figure 5A:
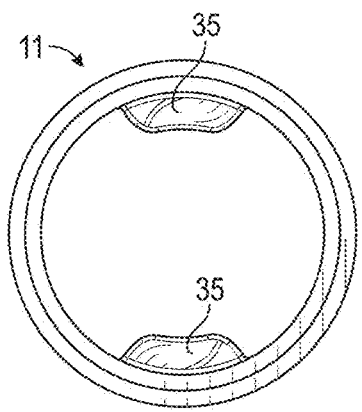
FIG. 5A-FIG. 5H shows seven different views ((a)-(h)) of the resilient inner body portion of a representative capping and cleansing device of the invention. Representative measurements of this particular embodiment are shown on several of the views.
Figure 5B:
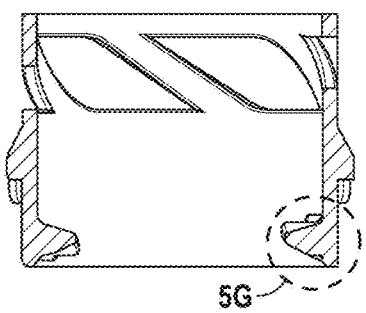
Figure 5C:
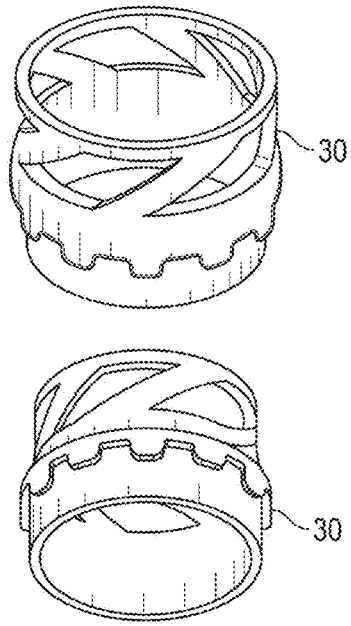
Figure 5D:
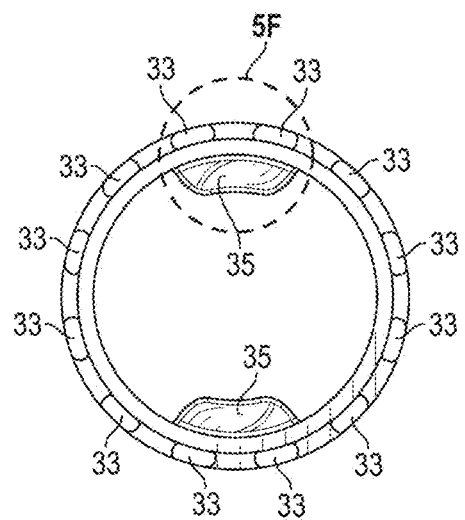
Figure 5E:
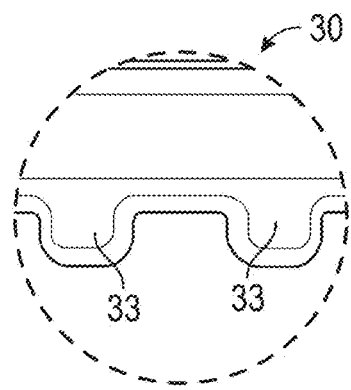
Figure 5F:
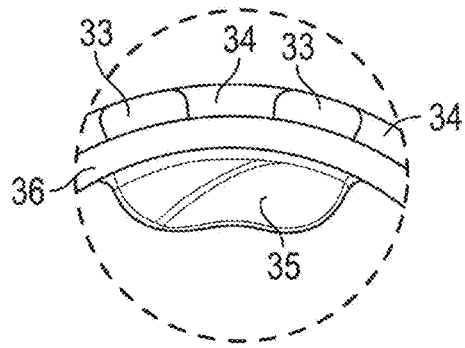
Figure 5G:
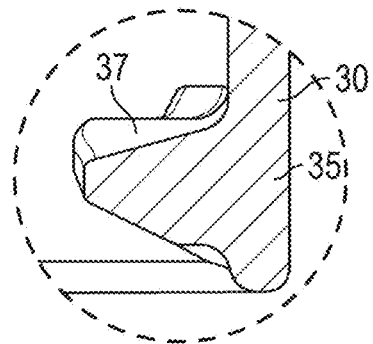
Figure 5H:
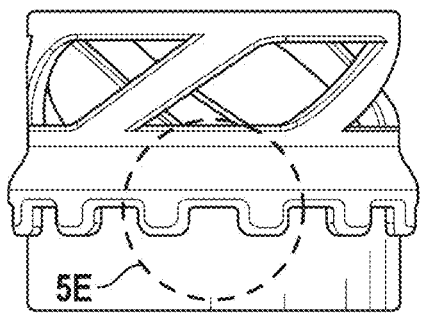
Figure 6A:
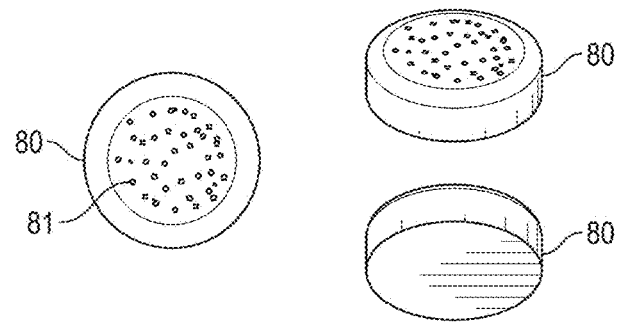
FIG. 6A-FIG. 6E shows five different views ((a)-(e)), three of which show a compressible cleansing matrix portion of a representative capping and cleansing device of the invention. Views (a)-(c) show top, side, and bottom views of this particular compressible cleansing matrix. Views (d) and (e) show bottom and side views of a seal portion of a representative capping and cleansing device of the invention.
Figure 6B:
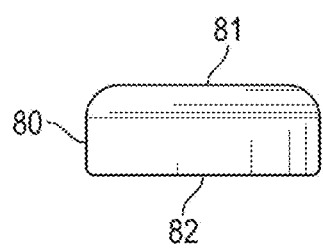
Figure 6C:
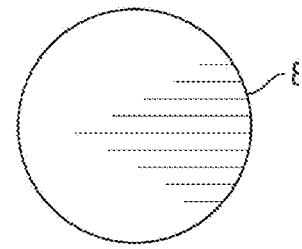
Figure 6D:
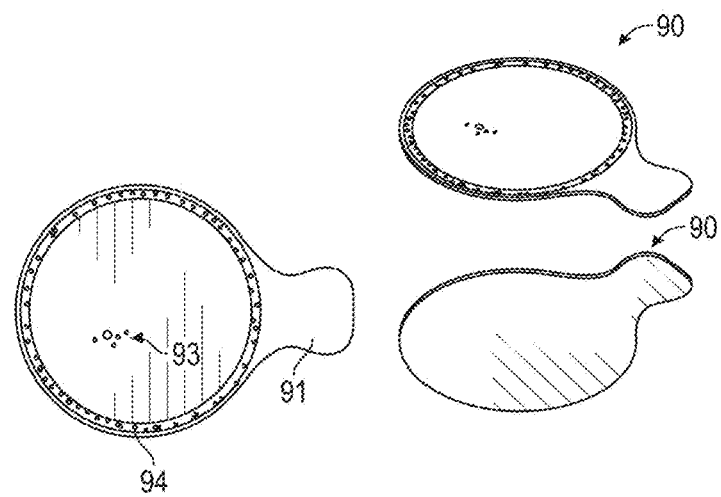
Figure 6E:
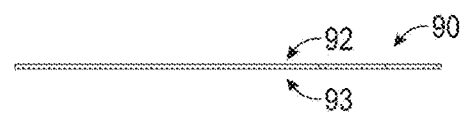

FIG. 4 shows views of the cap portion (11) of a representative capping and cleansing device (10) of the invention. View (a) shows a top view of the cap portion (11). Also visible on portions of the outer surface of the cap portion (11) are ridges and valleys that provide for enhanced friction, allowing a user to better grip or grasp the cap (10). View (b) shows a side view of the cap portion (11). View (c) shows a bottom view of the cap portion (11). Visible in this embodiment are six ribs (or protrusions) (18) evenly spaced (here, about 60 deg. on center) about the circumference of cap portion's inner surface. The ribs (18) are positioned and sized to engage complementary features on the outer surface of the resilient inner body (30)(not shown). The wall forming the matrix well (12) is also visible in this view. View (d) shows a cross-sectional view of the cap portion (11). The well (20) formed by the matrix well wall (12) that extends from the inner surface of the upper portion of the cap portion (11) is also represented, and is adapted to receive and retain the compressible cleansing matrix (80). In preferred embodiments, an adhesive (not shown) or other bonding reagent is used to adhere the compressible cleansing matrix (80) inside the well (20). The well (20) is spaced from the outer wall of the cap portion (11). The resulting space is sized and adapted for insertion of the resilient inner body (30), about which the cap portion (11) can be rotated when the complementary retaining elements (e.g., ribs (18) and teeth (33)) of the cap portion (11). In the representative embodiment of the inventive capping and cleansing device (10) depicted in the Figures, the upper surface (19) of the retaining elements (18) present in the cap portion (11) are designed to engage the lower surface of the locking grooves (34) between the teeth (33).

FIG. 5 shows seven different views ((a)-(h)) of the resilient inner body (30) of a representative capping and cleansing device of the invention (10). Representative measurements of this particular embodiment are shown on several of the views. Depicted in this embodiment are two thread tabs (35) disposed on the inner surface of the wall (36) of resilient inner body (30), 12 spaced teeth (33) to engage 12 complementary retaining elements (e.g., ribs (18)) on the inner surface of the cap portion (11). The resilient inner body (30) is adapted for compression by a user upon application of a suitable force, and rebound upon relieving of such pressure.

FIG. 6 shows five different views ((a)-(e)), three of which show a compressible cleansing matrix portion (80) of a representative capping and cleansing device of the invention (10). Views (a)-(c) show top, side, and bottom views of this particular compressible cleansing matrix (80). Preferably, the compressible cleansing matrix (80) is adhered using an adhesive to the surface of matrix well (20) of the cap portion (11). Views (d) and (e) of FIG. 6 show bottom and side views of a seal portion (90) of a representative capping and cleansing device of the invention. The seal (90) is typically sized to seal or cover the opening that allows access to the interior of the cap (10). Preferably, the seal contains one or more removal tabs (91) configured to allow grasping by a user such that the seal can be removed just prior to the device being used to cap and/or cleanse a needlefree connector (100). Preferably, the seal is adhered to the cap (10) using a suitable adhesive (94) applied to the inside surface (92) of the seal (90). The seal's outside surface (93) often will contain alphanumeric characters, bar code information, or the like.

FIG. 7 (FIGS. 7A-7E) shows five different views of another representative capping and cleansing device of the invention (300) in which a user engages the inner and outer housings (320, 301) by squeezing (or applying pressure using two or more fingers) the outer housing (301), causing it to deform slightly and move inner housing engaging elements (311) present on the inner surface of the outer housing's sidewall so that one or more them (typically on opposite sides of the outer housing (301)) engage outer housing engaging elements (326) present on the exterior surface of the inner housing (320) below the inner housing retaining element (322) on the outer surface of inner housing's sidewall (321). The top of the outer housing (309) integrates with the outer housing's sidewall (302). FIG. 7A shows an exploded perspective view of the device (outer housing (301), compressible cleansing matrix (305), and inner housing (320)) and an NC (100) to which the device (300) is to be connected (see FIGS. 7B, 7E). The NC (100) has threaded valve region (105) that includes a collar (101) below the threaded portion (102). The valve surface (110) is disposed on top of the threaded valve region (105). In FIGS. 7A-7E, the valve is not depicted.

FIG. 7B shows a perspective view of the assembled device (300) depicted in FIG. 7A secured to the threaded region of the valve portion (105) of the NC (100) depicted in FIG. 7A. Preferably, the plastic used to injection mold the outer housing (301) of the device (300) shown in this embodiment is softer than the plastic used to mold the inner housing (302). Preferably, the plastic used to form the outer housing is sufficiently pliable to allow it to be squeezed by a user to allow engagement of between the inner and outer housings' engaging elements (326, 311) for purposes of attaching and removing the device (300) from the NC (100) but resilient enough to allow the outer housing (301) to return to its original shape and thus allow the inner and outer housings' engaging elements (326, 311) to become disengaged. This allows a user to rotate the outer housing (301) and matrix 305) in relation to the NC (100) in order to cleanse its valve surface (110) when a cleansing operation is performed, for example, by rotating the device (300) without engaging the inner and outer housings' engaging elements (326, 311) a sufficient period of time (e.g., 1-15 seconds or more) and/or for a desired amount of rotation (e.g., 360 to 3,600 or more degrees) in the same or different directions.

FIG. 7C shows an exploded cross-section view of the components depicted in FIG. 7A. In addition, the thin, flexible lip seal (324) with a tapered profile integrated into the top surface of the inner housing (320) is designed to engage with the sealing surface (308) at the bottom of the matrix well, which includes a matrix cavity (303) into which matrix retaining ribs (307) protrude and allow rotational forces applied by a user to the device (300) to be translated to the compressible cleansing matrix (305). The threads (326) on the inner surface of the inner housing (320) are designed to engage the complementary threads (102) in the threaded region (105) of the NC (100).

As will be appreciated, and as shown in FIGS. 7C-7E, the compressible cleansing matrix (305) is inserted into the matrix well (303) during manufacture. The matrix (305) can be impregnated with a cleansing reagent (e.g., silver ions), and in preferred embodiments, a liquid disinfectant such as a 70% IPA solution. The bearing surface (323) of the outer housing retaining element (322), here a tapered flange molded as part of the inner housing (320) during manufacture, is designed to ride on the complementary bearing surfaces (310) disposed on the inner surface of the outer housing's main cavity (304). The inner housing retaining elements (306) of the outer housing (301) provide for retention of the inner housing (320) in the outer housing's main cavity (304) after the inner housing assembled into a functional subassembly with the outer housing during manufacture. For example, the inner housing may be urged into the outer housing with sufficient force to join them into a functional subassembly ready for insertion of compressible cleansing matrix (305) followed by instillation of a liquid disinfectant (e.g., a 70% IPA solution), sealing, packaging, and sterilization. The inner housing engaging elements (311) present on the inner surface of the outer housing's sidewall (302) allow the outer housing (302) to engage outer housing engaging elements (326) on the adjacent outer surface of the inner housing (320).

FIG. 7D, the cross section view shows the components of the device of the invention (outer housing (301), compressible cleansing matrix (305), and inner housing (320)) assembled into a functional capping and cleansing device (300) ready for attachment to the threaded region of the valve portion (105) of the NC depicted in FIG. 7A. When the device (300) is attached to an NC (100), the NC contacting surface of the matrix (305) contacts the valve surface (110) of the NC, allowing that surface to be cleansed by a user rotating the device (300) in relation to the NC. FIG. 7E is a cross section showing the capping and cleansing device (300) of the invention screwed onto the NC, which results compression of the compressible cleansing matrix (305) against the NC's valve surface (110).

FIG. 8 (FIGS. 8A-8E) shows five different views of another representative capping and cleansing device of the invention. This embodiment is similar to that depicted in FIG. 7 (FIGS. 7A-7E)m the difference being that in the embodiment shown in FIG. 8 the seal is not a lip seal (324) located on the inner housing (320) but a tapered, downwardly extending seal (408) disposed on the bottom surface of the component forming the matrix well (403) in the outer housing (401).

FIG. 8A shows an exploded perspective view of this device embodiment (400) (outer housing (401), compressible cleansing matrix (405), and inner housing (420)) and an NC (100) to which the device (400) is to be connected (see FIGS. 8B, 8E). FIG. 8B shows a perspective view of the assembled device (400) depicted in FIG. 8A secured to the threaded region of the valve portion (105) of the NC depicted in FIG. 8A. FIG. 8C shows an exploded cross-section view of the components depicted in FIG. 8A, while in FIG. 8D, the cross section view shows the components of the device of the invention (outer housing, compressible cleansing matrix, and inner housing) assembled into a functional capping and cleansing device ready for attachment to the threaded region of the valve portion of the NC depicted in FIG. 8A. FIG. 8E is a cross section showing the capping and cleansing device of the invention screwed onto the NC, which results compression of the compressible matrix against the NC's valve surface.

Specifically, FIG. 8 (FIGS. 8A-8E) shows five different views of another representative capping and cleansing device of the invention (400) in which a user engages the inner and outer housings (420, 401) by squeezing (or applying pressure using two or more fingers) the outer housing (401), causing it to deform slightly and move inner housing engaging elements (411) present on the inner surface of the outer housing's sidewall so that one or more them (typically on opposite sides of the outer housing (401)) engage outer housing engaging elements (426) present on the exterior surface of the inner housing (420) below the inner housing retaining element (422) on the outer surface of inner housing's sidewall (421). The top of the outer housing (409) integrates with the outer housing's sidewall (402). FIG. 8A shows an exploded perspective view of the device (outer housing (401), compressible cleansing matrix (405), and inner housing (420)) and an NC (100) to which the device (400) is to be connected (see FIGS. 8B, 8E). The NC (100) has threaded valve region (105) that includes a collar (101) below its threaded portion (102). The valve surface (110) is disposed on top of the threaded valve region (105). In FIGS. 8A-8E, the valve of the NC (100) is not depicted.

FIG. 8B shows a perspective view of the assembled device (400) depicted in FIG. 8A secured to the threaded region of the valve portion (105) of the NC (100) depicted in FIG. 8A. Preferably, the plastic used to injection mold the outer housing (401) of the device (400) shown in this embodiment is softer than the plastic used to mold the inner housing (402). Preferably, the plastic used to form the outer housing is sufficiently pliable to allow it to be squeezed by a user to allow engagement of between the inner and outer housings' engaging elements (426, 411) for purposes of attaching and removing the device (400) from the NC (100) but resilient enough to allow the outer housing (401) to return to its original shape and thus allow the inner and outer housings' engaging elements (426, 411) to become disengaged. This allows a user to rotate the outer housing (401) and matrix 405) in relation to the NC (100) in order to cleanse its valve surface (110) when a cleansing operation is performed, for example, by rotating the device (400) without engaging the inner and outer housings' engaging elements (426, 411) a sufficient period of time (e.g., 1-15 seconds or more) and/or for a desired amount of rotation (e.g., 360 to 3,600 or more degrees) in the same or different directions.

FIG. 8C shows an exploded cross-section view of the components depicted in FIG. 8A. In this embodiment (400), a tapered, downwardly extending seal element (408) is disposed on the bottom surface of the component forming the matrix well (403) in the outer housing (401). This seal (408) has a sealing surface 409 that is designed to seal against the sealing surface (423) of the tapered flange of the retaining element (422) of the inner housing (420). As in the embodiment depicted in FIG. 7, the embodiment depicted in FIG. 8 is tapered so as to allow the inner housing to be readily assembled with the outer housing (401), e.g., by application of sufficient pressure to the parts to cause the pliable, resilient outer housing to expand sufficiently to allow the inner housing (420) to be inserted into the outer housing's main cavity (404) to the point where the bearing surface (424) of the inner housing's retaining element (422) passes beyond the outer housing's inner housing retaining element (406), at which point the outer housing (401) contracts and the bearing surfaces (424, 410) of the inner and outer housings' retaining elements (422, 406) come into contact so as to prevent the inner housing (420) from being pulled out of the outer housing's main cavity (404) and to provide a smooth interface that allows easy, low friction rotation between the inner and outer housings (420, 401) if and when desired.

As will be appreciated, and as shown in FIGS. 8C-8E, the compressible cleansing matrix (405) is inserted into the matrix well (404) during manufacture. The matrix (405) can be impregnated with a cleansing reagent (e.g., silver ions), and in preferred embodiments, a liquid disinfectant such as a 70% IPA solution. The bearing surface (424) of the outer housing retaining element (422), here also a tapered flange molded as part of the inner housing (420) during manufacture, is designed to ride on the complementary bearing surfaces (410) disposed on the inner surface of the outer housing's main cavity (404). The inner housing retaining elements (411) of the outer housing (401) provide for retention of the inner housing (420) in the outer housing's main cavity (404) after the inner housing assembled into a functional subassembly with the outer housing during manufacture. For example, the inner housing may be urged into the outer housing with sufficient force to join them into a functional subassembly ready for insertion of compressible cleansing matrix 405) followed by instillation of a liquid disinfectant (e.g., a 70% IPA solution), sealing, packaging, and sterilization. The inner housing engaging elements (411) present on the inner surface of the outer housing's sidewall (402) allow the outer housing (401) to engage outer housing engaging elements (426) on the adjacent outer surface of the inner housing (420).

FIG. 8D, the cross section view shows the components of the device of the invention (outer housing (401), compressible cleansing matrix (405), and inner housing (420)) assembled into a functional capping and cleansing device (400) ready for attachment to the threaded region of the valve portion (105) of the NC depicted in FIG. 8A. When the device (400) is attached to an NC (100), the NC contacting surface of the matrix (405) contacts the valve surface (110) of the NC, allowing that surface to be cleansed by a user rotating the device (400) in relation to the NC. FIG. 8E is a cross section showing the capping and cleansing device (400) of the invention screwed onto the NC, which results compression of the compressible cleansing matrix (405) against the NC's valve surface (110).

FIG. 9 (FIGS. 9A-9E) shows five different views of another representative capping and cleansing device of the invention. This embodiment is similar to that depicted in FIG. 8 (FIGS. 8A-8E), the difference being that in the embodiment shown in FIG. 9 the outer housing (501) has a different outer configuration than the embodiment depicted in FIG. 8. Here, the sidewall (502) forming the structural portion of the device (500) has a step in it, giving it a layered, "wedding cake" appearance in profile. To make the device (500) easy for a user to grasp, a series of exterior ribs (535) are provided on the upper portion of the outer housing's exterior.

Specifically, FIG. 9 (FIGS. 9A-9E) shows five different views of another representative capping and cleansing device of the invention (500) in which a user engages the inner and outer housings (520, 501) by squeezing (or applying pressure using two or more fingers) the outer housing (501), causing it to deform slightly and move inner housing engaging elements (511) present on the inner surface of the outer housing's sidewall so that one or more them (typically on opposite sides of the outer housing (501)) engage outer housing engaging elements (526) present on the exterior surface of the inner housing (520) below the inner housing retaining element (522) on the outer surface of inner housing's sidewall (521). The top of the outer housing (509) integrates with the outer housing's sidewall (502). FIG. 9D shows an exploded perspective view of the device (outer housing (501), compressible cleansing matrix (505), and inner housing (520)) and an NC (100) to which the device (500) is to be connected (see FIGS. 9B, 9C). The NC (100) has threaded valve region (105) that includes a collar (101) below its threaded portion (102). The valve surface (110) is disposed on top of the threaded valve region (105). In FIGS. 9A-9E, the valve of the NC (100) is not depicted.

FIG. 9A shows a perspective view of the assembled device (500) depicted in FIG. 9D secured to the threaded region of the valve portion (105) of the NC (100) depicted in FIG. 9A. Preferably, the plastic used to injection mold the outer housing (501) of the device (500) shown in this embodiment is softer than the plastic used to mold the inner housing (502). Preferably, the plastic used to form the outer housing is sufficiently pliable to allow it to be squeezed by a user to allow engagement of between the inner and outer housings' engaging elements (526, 511) for purposes of attaching and removing the device (500) from the NC (100) but resilient enough to allow the outer housing (501) to return to its original shape and thus allow the inner and outer housings' engaging elements (526, 511) to become disengaged. This allows a user to rotate the outer housing (501) and matrix 505) in relation to the NC (100) in order to cleanse its valve surface (110) when a cleansing operation is performed, for example, by rotating the device (500) without engaging the inner and outer housings' engaging elements (526, 511) a sufficient period of time (e.g., 1-15 seconds or more) and/or for a desired amount of rotation (e.g., 360 to 3,600 or more degrees) in the same or different directions.

FIG. 9D shows an exploded cross-section view of the components depicted in FIGS. 9A-9C. In this embodiment (500), a tapered, downwardly extending seal element (508) is disposed on the bottom surface of the component forming the matrix well (503) in the outer housing (501). This seal (508) has a sealing surface 509 that is designed to seal against the sealing surface (523) of the tapered flange of the retaining element (522) of the inner housing (520). As in the embodiments depicted in FIGS. 7 and 8, the embodiment depicted in FIG. 9 is tapered so as to allow the inner housing to be readily assembled with the outer housing (501), e.g., by application of sufficient pressure to the parts to cause the pliable, resilient outer housing to expand sufficiently to allow the inner housing (520) to be inserted into the outer housing's main cavity (504) to the point where the bearing surface (524) of the inner housing's retaining element (522) passes beyond the outer housing's inner housing retaining element (506), at which point the outer housing (401) contracts and the bearing surfaces (524, 510) of the inner and outer housings' retaining elements (522, 506) come into contact so as to prevent the inner housing (520) from being pulled out of the outer housing's main cavity (504) and to provide a smooth interface that allows easy, low friction rotation between the inner and outer housings (520, 501) if and when desired.

As will be appreciated, and as shown in FIGS. 9B-9E, the compressible cleansing matrix (505) is inserted into the matrix well (504) during manufacture. The matrix (505) can be impregnated with a cleansing reagent (e.g., silver ions), and in preferred embodiments, a liquid disinfectant such as a 70% IPA solution. The bearing surface (524) of the outer housing retaining element (522), here also a tapered flange molded as part of the inner housing (520) during manufacture, is designed to ride on the complementary bearing surfaces (510) disposed on the inner surface of the outer housing's main cavity (504). The inner housing retaining elements (511) of the outer housing (501) provide for retention of the inner housing (520) in the outer housing's main cavity (504) after the inner housing assembled into a functional subassembly with the outer housing during manufacture. For example, the inner housing may be urged into the outer housing with sufficient force to join them into a functional subassembly ready for insertion of compressible cleansing matrix (505) followed by instillation of a liquid disinfectant (e.g., a 70% IPA solution), sealing, packaging, and sterilization. The inner housing engaging elements (511) present on the inner surface of the outer housing's sidewall (502) allow the outer housing (501) to engage outer housing engaging elements (526) on the adjacent outer surface of the inner housing (520).

FIG. 9D, the cross section view shows the components of the device of the invention (outer housing (501), compressible cleansing matrix (505), and inner housing (520)) assembled into a functional capping and cleansing device (500) ready for attachment to the threaded region of the valve portion (105) of the NC. When the device (500) is attached to an NC (100), the NC contacting surface of the matrix (505) contacts the valve surface (110) of the NC, allowing that surface to be cleansed by a user rotating the device (500) in relation to the NC. FIG. 8E is a cross section showing the capping and cleansing device (500) of the invention screwed onto the NC, which results compression of the compressible cleansing matrix (505) against the NC's valve surface (110).

Figure 10B:
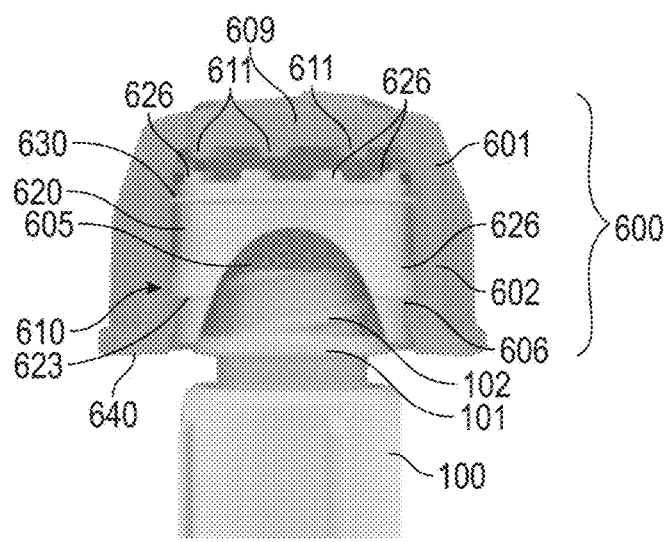
Figure 10C:
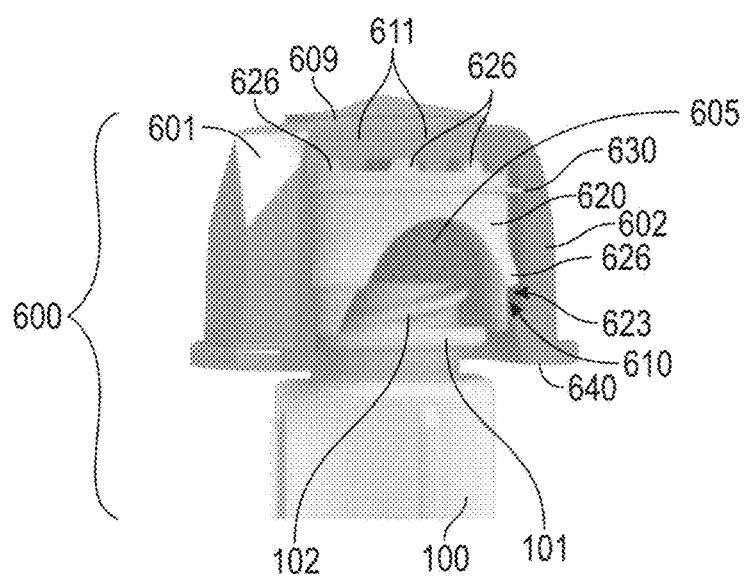

FIG. 10 shows three different cut-away views of another representative capping and cleansing device (600) of the invention in which the outer housing (601) is pushed upward by the compressible cleansing matrix (605) when the device (600) is screwed onto the threaded valve region (105) of a needlefree connector (100). That upward movement places the outer housing (601) in a neutral position where the engaging elements (611, 626) of the outer and inner housings (601, 620) are disengaged, allowing the outer housing (601) to be rotated in relation to the inner housing (620). FIGS. 10B and 10C show the device (600) secured to the threaded region of the valve portion (105) of an NC, while FIG. 10A shows the device (600) disconnected from the NC (100). FIG. 10B shows the outer housing of the device in a neutral position (the engaging elements of the inner and outer housings are not engaged), from which a user could rotate the outer housing (and compressible cleansing matrix) in relation to the inner housing and NC, to which the inner housing is secured. As will be appreciated, the compressible cleansing matrix (605) can serve as a spring or biasing element that, in the absence of a sufficient counteracting downward force, pushes the outer housing (601) up in relation to the inner housing (620), allowing a user to rotate the outer housing (and compressible cleansing matrix) in relation to the inner housing (620) and NC if and when desired. Absent such rotation, while connected to the NC the capping and cleansing device of the invention (600) serves as a cap to protect the threaded valve region (105) of the NC from environmental contamination, including microbial contamination. FIG. 10C depicts the device (600) when the engaging elements (626, 611) of the inner and outer housings (620, 601) are engaged, allowing the device to be screwed onto or off of the NC (100).

In the embodiment depicted in FIG. 10, the device (600) also includes a seal (630) disposed on the outer surface of the inner housing (620). The purpose of this seal is to prevent rapid loss of liquid cleansing reagents from the device once it has been attached to an NC, as it is preferred that a device according the invention be capable of remaining attached to an NC for up to 7 or more days.

As will be appreciated, in FIGS. 7-10, the lower surfaces (340, 440, 540, 640) of sidewall of outer housing (301, 401, 501, 601) are surfaces adapted to receive a lid or seal (not shown) to seal the interior spaces of the devices (300, 400, 500, 600) from the external environment. This not only allows retention of cleansing reagents in the compressible cleansing matrices (320, 420, 520, 620) until the particular is used to cap and/or cleanse a needlefree connector, but also to maintain the device's sterility.

Unless the context clearly requires otherwise, throughout the description above and the appended claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list.

The foregoing description, for purpose of explanation, has been described with reference to specific embodiments. However, the illustrative discussions above are not intended to be exhaustive or to limit the invention to the precise forms disclosed. Many modifications and variations are possible in view of the above descriptions. The embodiments were chosen and described in order to best explain the principles of the invention and its practical applications to thereby enable others skilled in the art to best utilize the invention and various embodiments with various modifications as are suited to the particular use contemplated. As such, the invention extends to all functionally equivalent structures, methods, and uses, such as are within the scope of the appended claims, and it is intended that the invention be limited only to the extent required by the applicable rules of law.

What is claimed is:

1. A capping and cleansing device for a threaded valve portion of a needlefree vascular access connector, the capping and cleansing device comprising:
   (a) an inner housing rotatably disposed in an outer housing, wherein the inner housing comprises a sidewall that bounds a central bore comprising oppositely disposed first and second openings, wherein the central bore is configured to allow the capping and cleansing device to be screwed onto and unscrewed from the threaded valve portion of the needlefree vascular access connector and into which a compressible cleansing matrix attached to the outer housing protrudes into the central bore to allow contact with a valve surface of the threaded valve portion of the needlefree vascular access connector when the capping and cleansing device is screwed onto the threaded valve portion of the needlefree vascular access connector;
   (b) the outer housing, wherein the outer housing comprises a cavity in which the inner housing is rotatably disposed, wherein the outer housing is configured to (A) retain and (B) engage and disengage from the inner housing so as to allow the outer housing to (i) retain the inner housing and be rotated independently of the inner housing at least 360 degrees in both a clockwise direction and a counter-clockwise direction by a user when the outer housing is not engaging the inner housing and (ii) retain the inner housing and be rotated in unison with the inner housing by the user when the outer housing and the inner housing are engaged; and
   (c) the compressible cleansing matrix attached to the outer housing and that protrudes into the cavity of the outer housing and into the central bore of the inner housing, wherein the compressible cleansing matrix rotates with the outer housing, wherein the compressible cleansing matrix is impregnated with a liquid disinfectant.

2. The capping and cleansing device according to claim 1 that further comprises a removable seal to seal the cavity of the outer housing from an external environment.

3. The capping and cleansing device according to claim 1, wherein the liquid disinfectant comprises isopropyl alcohol.

4. The capping and cleansing device according to claim 1, wherein the outer housing comprises an outer surface having a plurality of vertical ridges.

5. A method of cleansing a needlefree vascular access connector, comprising:
   (a) connecting a threaded valve portion of the needlefree vascular access connector to the capping and cleansing device according to claim 1 such that one or more surfaces of the threaded valve portion of the needlefree vascular access connector engage and at least partially compress the compressible cleansing matrix of the capping and cleansing device; and
   (b) rendering the outer housing of the capping and cleansing device rotatable in relation to the inner housing and rotating the outer housing in relation to the inner housing and the needlefree vascular access connector, thereby cleansing the one or more surfaces of the needlefree vascular access connector contacted by the compressible cleansing matrix of the capping and cleansing device.

6. The method according to claim 5 that further comprises leaving the needlefree vascular access connector connected to the capping and cleansing device after cleansing, thereby capping the threaded valve portion of the needlefree vascular access connector.

7. The capping and cleansing device according to claim 1, wherein the liquid disinfectant comprises a 70% isopropyl alcohol solution.

8. A capping and cleansing device for a threaded valve portion of a needlefree vascular access connector, the capping and cleansing device comprising:
   (a) an inner housing that comprises: a substantially cylindrical sidewall that forms a central bore comprising a top end oppositely disposed from a bottom end, wherein the top end comprises a top opening and the bottom end comprises a bottom opening, wherein proximate to the bottom opening and disposed on an inner surface of the central bore are one or more thread-engaging tabs or threads configured to releasably engage the threaded valve portion of the needlefree vascular access connector; an outer housing-engaging region configured to provide releasable mechanical engagement of an outer housing of the capping and cleansing device; and an outer housing-retaining region configured to retain the inner housing in a cavity of the outer housing and allow at least 360 degrees of rotation in both a clockwise direction and a counter-clockwise direction of the outer housing in relation to the inner housing when the outer housing-engaging region is not engaged;
   (b) the outer housing, wherein the outer housing comprises the cavity formed by an outer wall and a top wall, a concentric matrix well, at least one inner housing engaging structure and at least one inner housing retaining structure configured to, respectively, releasably engage and retain the inner housing in the cavity, wherein when the at least one inner housing engaging structure engages the inner housing, the inner and outer housings can rotate in unison and wherein when the at least one inner housing engaging structure of the outer housing does not engage the inner housing, the outer housing can rotate in relation to the inner housing; and
   (c) a compressible cleansing matrix that comprises a liquid cleansing reagent disposed therein and which is secured in the matrix well of the outer housing, wherein the compressible cleansing matrix is configured to contact and cleanse one or more surfaces of the threaded valve portion of the needlefree vascular access connector when the capping and cleansing device is secured to the threaded valve portion of the needlefree vascular access connector and the outer housing and the compressible cleansing matrix are rotated in relation to the inner housing.

9. The capping and cleansing device according to claim 8 that further comprises a removable seal to seal the cavity of the capping and cleansing device from an external environment.

10. The capping and cleansing device according to claim 8, wherein the liquid cleansing reagent comprises isopropyl alcohol.

11. The capping and cleansing device according to claim 8, wherein the outer housing comprises an outer surface having a plurality of vertical ridges.

12. A method of cleansing a needlefree vascular access connector, comprising:
   (a) connecting a threaded valve portion of the needlefree vascular access connector to the capping and cleansing device according to claim 7 such that one or more surfaces of the threaded valve portion of the needlefree vascular access connector engage and at least partially compress the compressible cleansing matrix of the capping and cleansing device; and
   (b) rendering the outer housing of the capping and cleansing device rotatable in relation to the inner housing and rotating the outer housing in relation to the inner housing and the needlefree vascular access connector, thereby cleansing the one or more surfaces of the needlefree vascular access connector contacted by the compressible cleansing matrix of the capping and cleansing device.

13. The method according to claim 12 that further comprises leaving the needlefree vascular access connector connected to the capping and cleansing device after cleansing, thereby capping the threaded valve portion of the needlefree vascular access connector.

14. The capping and cleansing device according to claim 8, wherein the liquid cleansing reagent comprises a 70% isopropyl alcohol solution.

* * * * *